(12) United States Patent
Hulvershorn et al.

(10) Patent No.: US 12,048,399 B2
(45) Date of Patent: Jul. 30, 2024

(54) DEVICES, SYSTEMS, AND METHODS FOR DISPENSING A FLUID

(71) Applicant: Blink Device, LLC, Seattle, WA (US)

(72) Inventors: Justin Hulvershorn, Seattle, WA (US); Daniel Hoffman, Seattle, WA (US)

(73) Assignee: Blink Device, LLC, Seattle, WA (US)

( * ) Notice: Subject to any disclaimer, the term of this patent is extended or adjusted under 35 U.S.C. 154(b) by 259 days.

(21) Appl. No.: 17/633,923

(22) PCT Filed: Jul. 24, 2020

(86) PCT No.: PCT/US2020/043574
§ 371 (c)(1),
(2) Date: Feb. 8, 2022

(87) PCT Pub. No.: WO2021/030032
PCT Pub. Date: Feb. 18, 2021

(65) Prior Publication Data
US 2022/0287515 A1 Sep. 15, 2022

Related U.S. Application Data

(60) Provisional application No. 62/886,662, filed on Aug. 14, 2019.

(51) Int. Cl.
*A47K 5/12* (2006.01)
*G06Q 10/06* (2023.01)
*G06Q 10/0631* (2023.01)
*G16H 20/13* (2018.01)
*A61L 9/00* (2006.01)

(52) U.S. Cl.
CPC .......... *A47K 5/1217* (2013.01); *A47K 5/1202* (2013.01); *G06Q 10/06311* (2013.01); *G16H 20/13* (2018.01); *A61L 9/00* (2013.01)

(58) Field of Classification Search
CPC ............... A47K 5/1217; A47K 5/1202; G06Q 10/06311; A61L 9/00; G16H 20/13
See application file for complete search history.

(56) References Cited

U.S. PATENT DOCUMENTS 5,927,548 A * 7/1999 Villaveces ................ A45F 5/02
222/325
6,392,546 B1 5/2002 Smith
(Continued)

OTHER PUBLICATIONS

International Search Report and Written Opinion issued in related International Patent Application No. PCT/US2020/043574, issued on on Oct. 9, 2020 (15 pages, in English).
(Continued)

*Primary Examiner* — Frederick C Nicolas
(74) *Attorney, Agent, or Firm* — Bookoff McAndrews, PLLC

(57) ABSTRACT

Portable sanitization fluid dispensing devices, systems including such devices, and methods for using such devices are described herein. Such devices, systems, and methods may assist in ensuring proper hand sanitization in sensitive environments, such as medical facilities, laboratories, food and drug preparation facilities, and the like. Devices and systems disclosed herein may be adaptive to, e.g., changing schedules, different users, and different environments.

20 Claims, 10 Drawing Sheets

(56) References Cited

U.S. PATENT DOCUMENTS

| | | | | |
|---|---|---|---|---|
| 7,825,812 B2* | 11/2010 | Ogrin | ................... | G08B 21/245 |
| | | | | 340/539.11 |
| 8,844,766 B2* | 9/2014 | Zaima | ................... | G16H 40/20 |
| | | | | 222/162 |
| 11,717,063 B1* | 8/2023 | Demirjian | .............. | G04B 47/00 |
| | | | | 222/175 |
| 2007/0229288 A1 | 10/2007 | Ogrin et al. | | |
| 2010/0094581 A1 | 4/2010 | Cagle | | |
| 2015/0199883 A1 | 7/2015 | Hartley et al. | | |
| 2016/0309967 A1 | 10/2016 | Pelfrey et al. | | |
| 2018/0257921 A1 | 9/2018 | Li et al. | | |
| 2022/0287515 A1* | 9/2022 | Hulvershorn | ........ | A47K 5/1217 |

OTHER PUBLICATIONS

Hyppa, Connor, et al. "Anesthesiologist Hand Hygiene." College of Engineering, University of Washington, at least as of Jun. 17, 2019. Poster. (1 page, in English).

* cited by examiner

DEVICES, SYSTEMS, AND METHODS FOR DISPENSING A FLUID

CROSS-REFERENCE TO RELATED APPLICATIONS

This application is the national stage entry of International Patent Application No. PCT/US2020/043574, filed on Jul. 24, 2020, which claims priority to U.S. Provisional Application No. 62/886,662, filed on Aug. 14, 2019, which are incorporated by reference herein in their entirety.

FIELD OF DISCLOSURE

Various embodiments of the present disclosure relate to, among other things, portable sanitization agent (e.g., a fluid) dispensing devices, systems incorporating such devices, and methods for using such devices. Some embodiments of the present disclosure relate, for example, to providing reminders to a user from a portable sanitization agent dispensing device, dispensing sanitization agent from the device in response to a trigger, and tracking and adapting to usage of the device.

INTRODUCTION

Regular and thorough hand sanitization is a priority in various environments, such as medical facilities, food and drug preparation facilities, laboratories, and in other environments in which there is a particular interest in preventing bacteria, viruses, and/or other microbes or contaminants from lingering or spreading. In some such environments, and in some cases, maintaining regular hand sanitization habits also may be challenging, for various reasons. For example, in some environments, hand sanitization devices (e.g., stationary devices, such as wall-mounted devices, in hospitals and/or laboratories) may not be optimally located for regular, intermittent use. In some environments, placement of stationary hand sanitization devices may not be practical or desirable. Moreover, adherence to rules for periodic hand sanitization may be difficult for individuals who are otherwise occupied with time sensitive tasks, such as triage, surgeries, patient care, laboratory procedures, food preparation procedures, and the like.

Additionally, overuse of hand sanitization agents, such as, e.g., sanitation fluids, may result in waste of sanitization fluid/devices and greater expense, while underuse may result in inadequate adherence to standards of care or operation. Moreover, different individuals within an environment may require the use of different quantities of hand sanitization fluid, and/or may require the use of hand sanitization fluid at different times or intervals. In some cases, their needs and schedules, including portions of their schedules requiring regular hand sanitization, may change over time.

SUMMARY

Aspects of the present disclosure are directed to methods for dispensing sanitization fluid from portable electronic sanitization fluid dispensing devices. In one aspect, a method for dispensing sanitization fluid from a portable electronic sanitization fluid dispensing device includes: receiving, at the device, a fluid dispensing reminder schedule; receiving, at the device, identifying information of a user; receiving, at the device, data indicating an event for which fluid dispensing is recommended; generating, from the device, a fluid dispensing reminder; and, in response to receiving a trigger, dispensing a volume of sanitization fluid, wherein the volume of sanitization fluid is automatically selected based on an event type, a trigger type, or the identifying information of the user.

In some examples, the identifying information of a user includes at least one of a user role within an institution, and a user hand size. In some examples, the event type includes at least one of entering a patient area, starting a patient procedure, completing a patient procedure, touching a patient, and touching patient surroundings. In some examples, the event type includes entering a patient area, and the method further includes altering a frequency of fluid dispensing reminders from the device based on the patient area. In some examples, the data indicating an event for which fluid dispensing is recommended includes data indicating proximity to a sensor. In some examples, the event type includes a passage of an amount of time since a volume of sanitization fluid was previously dispensed from the device, wherein passage of an amount of time lower than a threshold time results in dispensing a first volume of sanitization fluid from the device, and passage of an amount of time greater than the threshold time results in dispensing a second volume of sanitization fluid from the device greater than the first volume.

In some examples, the trigger type includes one of a proximity sensor trigger, an auditory cue, a motion cue, or one or more tactile cues. In some examples, the auditory trigger includes a voice command. In some examples, the trigger type includes one or more tactile triggers, and the method further comprises, in response to receiving, at the device, a first number of tactile triggers within a predetermined time, dispensing a first volume of sanitization fluid from the device, and in response to receiving, at the device, a second number of tactile triggers within the predetermined time, dispensing a second volume of sanitization fluid from the device.

In one aspect, a method for generating a customized fluid dispensing reminder schedule for a portable electronic fluid dispensing device includes: receiving a fluid dispensing reminder schedule; receiving identifying information for a device user; using the identifying information, revising the fluid dispensing reminder schedule; and sending the revised fluid dispensing reminder schedule to the device. In some examples, the identifying information for the device user includes a user schedule. In some examples, the identifying information for the device user includes a user hand size. In some examples, the method further includes: receiving, from the device, fluid dispensing records; using the fluid dispensing records, further revising the fluid dispensing reminder schedule; and sending the further revised fluid dispensing reminder schedule to the device.

In one aspect, a method for updating a fluid dispensing reminder schedule includes: sending, to a portable electronic fluid dispensing device, a first fluid dispensing reminder schedule; receiving, from the device, data reflecting fluid dispensing in response to reminders; tuning a machine learning algorithm using the received data; using the tuned machine learning algorithm, updating the fluid dispensing reminder schedule; and sending, to the device, the updated fluid dispensing reminder schedule. In some examples, the data reflecting fluid dispensing in response to reminders includes data showing that fluid was not dispensed in response to one or more reminders, and the updated fluid dispensing reminder schedule includes a reduced number of fluid dispensing reminders in comparison to the first fluid dispensing reminder schedule. In some examples, the data reflecting fluid dispensing in response to reminders includes data showing that fluid was dispensed more frequently than a frequency of reminders generated by the device; and the updated fluid dispensing reminder schedule includes an increased number of fluid dispensing reminders in comparison to the first fluid dispensing reminder schedule. In some examples, the method further includes generating the first fluid dispensing reminder schedule using the machine learning algorithm, wherein the machine learning algorithm is trained using a plurality of fluid dispensing schedules.

In one aspect of the present disclosure, a portable electronic fluid dispensing device system includes a portable device, which itself includes: a cartridge comprising a cavity for holding sanitization fluid; a pump configured to pump sanitization fluid out of the cartridge; a reminder generator; an identification chip; a dispensing trigger configured to actuate the pump when activated; and a portable wireless communication module. The system also includes a base station, which itself includes: a charging port for the portable device; a wireless communication module configured to communicate wirelessly with the portable wireless communication module; and an identification chip reader. In some examples, the dispensing trigger is activated by one of an auditory cue or a tactile cue. In some examples, the system further includes a triggering device, wherein proximity of the portable device to the triggering device activates the dispensing trigger.

In a further aspect of the present disclosure, a portable electronic fluid dispensing device includes: a fluid-containing cartridge; a trigger; and an electronic pump, comprising: a pressure sensor configured to sense a fluid pressure in the cartridge; a timer; and a pump outlet fluidly connected with an interior of the cartridge, wherein the device is operable independently of a fixed power source. In some examples, the trigger is a tactile trigger. In some examples, the cartridge is disposable. In some examples, a system includes a plurality of base stations, wherein each base station is paired to the device. In some examples, each base station is a mobile device configured to transmit a user command to the device for adjusting one or more settings. In some examples, each base station is configured to receive usage data from the device and to send the usage data to a cloud computing system.

In some examples, the base station includes a mobile application configured to compute one or more gel dispensing metrics. In some examples, the device further includes a processing component programmed to receive an input from the trigger and, in response, actuate the electronic pump to dispense a volume of fluid from the cartridge. In some examples, the trigger is a tactile trigger, and the input is a number of touches received at the tactile trigger.

In a further aspect, a method is disclosed for dispensing sanitization fluid from a portable electronic fluid dispensing device having an electronic pump and a fluid-containing cartridge. The method includes: receiving, at the device, a trigger; in response to the received trigger, activating the electronic pump; measuring a pressure in the fluid-containing cartridge; and deactivating the electronic pump after a time interval, wherein the time interval is determined using the measured pressure and an elapsed time since the pump was activated, and wherein the electronic pump, when active for the time interval, causes a predetermined volume of sanitization fluid to be dispensed from the fluid-containing cartridge.

In some examples, the trigger type includes: a proximity sensor trigger; an auditory cue; a motion cue; or one or more tactile cues. In some examples, measuring the pressure in the fluid-containing cartridge comprises measuring an increase in pressure caused by the electronic pump. In some examples, the predetermined volume of sanitization fluid is determined using the received trigger. In some examples, the device further includes a pressure release valve coupled to the fluid-containing cartridge, wherein the pressure release valve is configured to control the pressure in the fluid-containing cartridge. In some examples, the pressure release valve includes a solenoid configured to generate an electric field or voltage within the fluid-containing cartridge to return an interior of the fluid-containing cartridge to atmospheric pressure. In some examples, the solenoid is configured to activate in response to deactivating the electronic pump after the time interval.

In a further aspect, a method is disclosed for updating a fluid dispensing reminder schedule. The method includes: sending, to a portable electronic fluid dispensing device, a first fluid dispensing reminder schedule; receiving, from a mobile device, data of a geolocation of the mobile device; tuning a machine learning algorithm using the received data; using the tuned machine learning algorithm, updating the fluid dispensing reminder schedule; and sending, to the portable electronic fluid dispensing device, the updated fluid dispensing reminder schedule.

In some examples, the data of the geolocation is indicative of a high-risk area such that tuning the machine learning algorithm includes increasing a frequency of reminders included in the fluid dispensing reminder schedule. In some examples, the data of the geolocation is indicative of a low-risk area such that tuning the machine learning algorithm includes decreasing a frequency of reminders included in the fluid dispensing reminder schedule.

In a further aspect, a method is disclosed for updating a fluid dispensing mode. The method includes: sending, to a portable electronic fluid dispensing device, a plurality of fluid dispensing modes, each of the fluid dispensing modes include one or more settings; receiving, from a mobile device, data of a geolocation of the mobile device; activating at least one of the plurality of fluid dispensing modes on the portable electronic fluid dispensing device based on the received data; and changing the one or more settings of the portable electronic fluid dispensing device based on the at least one of the plurality of fluid dispensing modes. In some examples, the one or more settings include a fluid dispensing volume and a fluid dispensing reminder.

BRIEF DESCRIPTION OF THE DRAWINGS

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

Figure 1:
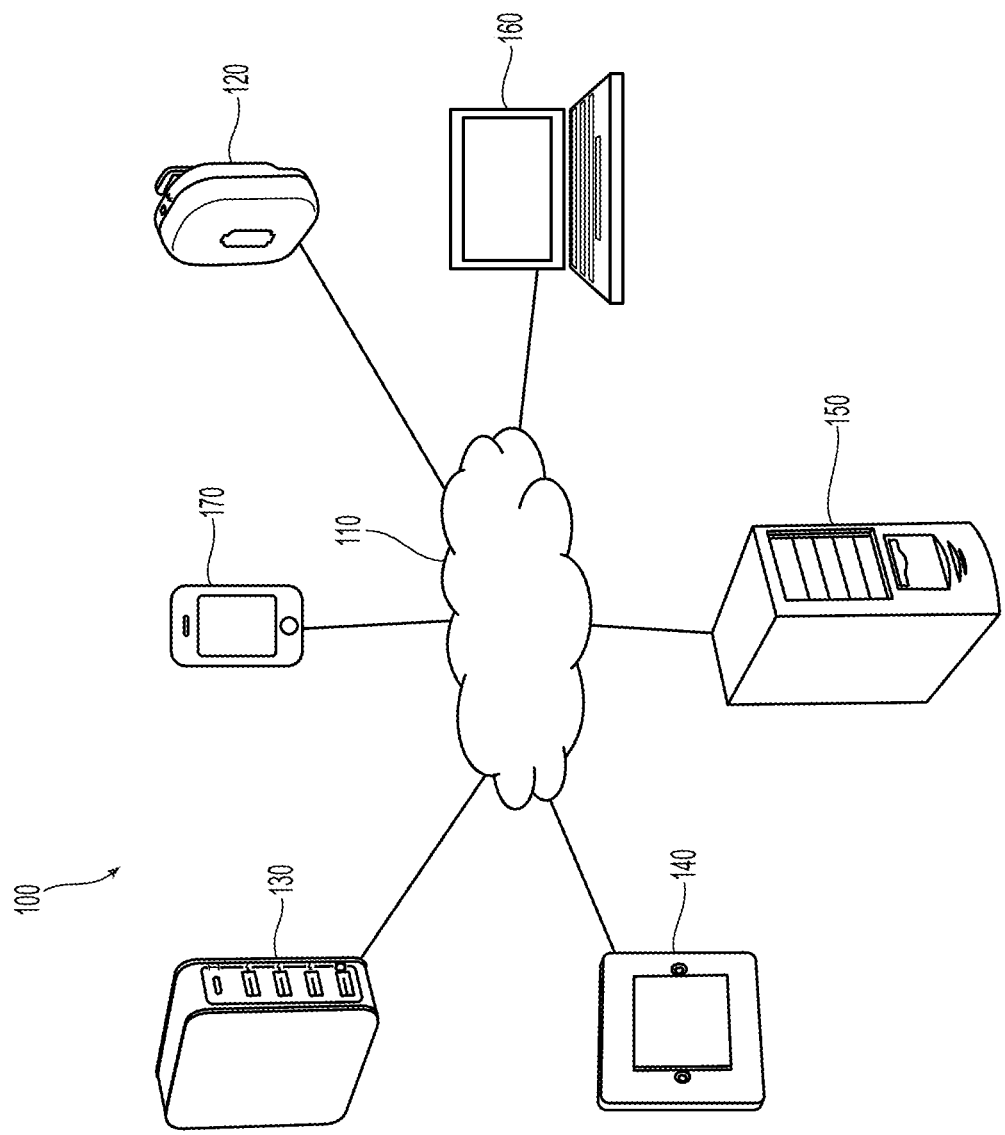
FIG. 1 depicts an exemplary system in which devices and methods of the present disclosure may operate.

There are many embodiments described and illustrated herein. The present disclosure is not limited to any single aspect or embodiment thereof, nor is it limited to any specific combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

Aspects of the present disclosure are described in greater detail below. The terms and definitions as used and clarified herein are intended to represent the meaning within the present disclosure. The terms and definitions provided herein control, if in conflict with terms and/or definitions incorporated by reference.

It should be noted that the description set forth herein is merely illustrative in nature and is not intended to limit the embodiments of the subject matter, or the application and uses of such embodiments. Any implementation described herein as exemplary is not to be construed as preferred or advantageous over other implementations. Rather, the term "exemplary" is used in the sense of example or "illustrative," rather than "ideal." The terms "comprise," "include," "have," "with," and any variations thereof are used synonymously to denote or describe a non-exclusive inclusion. As such, a device or a method that uses such terms does not include only those elements or steps, but may include other elements and steps not expressly listed or inherent to such device and method. Further, the terms "first," "second," and the like, herein do not denote any order, quantity, or importance, but rather are used to distinguish one element from another. Similarly, terms of relative orientation, such as "top," "bottom," etc. are used with reference to the orientation of the structure illustrated in the figures being described. Moreover, the terms "a" and "an" herein do not denote a limitation of quantity, but rather denote the presence of at least one of the referenced item. The terms "about" or "approximately" as used herein with respect to a value may refer to a variation of 10% above or below the stated value.

While a number of objects and advantages of the embodiments disclosed herein (and variations thereof) are described, not necessarily all such objects or advantages may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Generally, aspects of the present disclosure may assist in improving the convenience and use of sanitization agents (e.g., hand sanitization fluids). For example, aspects of the present disclosure may be configured to assist a user in using a sanitization agent regularly, to track a user's usage of a sanitization agent, to generate reminders to use a volume of sanitization fluid at regular intervals or in accordance with a schedule, to adaptively remind a user to use a sanitization agent depending on a particular user's schedule, habits, responsibilities, etc., to dispense a suitable volume of a sanitization fluid to a user depending on a characteristic of the user, a dispensing schedule, or an event, and/or to generate feedback to a user or institution about sanitization agent usage. Moreover, aspects of the present disclosure may be configured to accomplish any and/or all of the above goals, while also assisting in improving periodic availability of suitable amounts of sanitization agent to a user over a period of time, such as over a day, over a period of a work shift (e.g., an 8-hour or 12-hour shift), or over a period of a particular procedure or endeavor (e.g., a medical procedure, a laboratory procedure, etc.).

As used herein, the term "sanitization agent" or "sanitization fluid" may refer to any gel, liquid, aerosol, cream, or the like that may be dispensed and used for sanitization of human skin. Sanitization agents may include fluids that may include one or more sanitization ingredients, such as an alcohol (e.g., ethyl alcohol) benzalkonium chloride, or other sanitizing ingredients. In some embodiments, a sanitization agent may include an antimicrobial compound, such as triclosan. Sanitization agent may also include other ingredients, such as water, emulsifiers, foaming agents, fragrances, and/or glycerin. Generally, a sanitization agent may be prepared such that it has a known concentration of a sanitization ingredient, and a corresponding recommended minimum volume to be dispensed in a single use to ensure sanitization of the hands when properly applied. For example, commonly recommended minimum volumes of a single use of a sanitization agent include, e.g., from about 0.2 mL to about 2.0 mL, such as from about 0.5 mL to about 2.0 mL, or from about 0.8 mL to about 1.5 mL, such as about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, or about 2.0 mL. In some embodiments, a recommended minimum volume for a single use of a sanitization fluid is 1.1 mL. Other recommended minimum volumes that are greater or smaller than the volumes specified here are also contemplated herein.

A minimum volume of sanitization fluid needed to sanitize the hands may depend on variable factors, such as the size of a user's hands (e.g., smaller hands may require a smaller volume), or an amount of time since the hands were previously sanitized (e.g., more recently-sanitized hands may require a smaller volume to become fully sanitized again). However, such factors commonly may not be tracked, and thus may not be incorporated into a recommendation. As is described further elsewhere herein, devices, systems, and methods of the present disclosure may assist in incorporating such factors into the dispensing of a volume of sanitization fluid into a user's hands. Advantageously, this may assist in preventing the over-use or under-use of sanitization fluids, thereby helping to ensure hands are fully sanitized while simultaneously reducing waste, expense, and/or development of sanitizer-immune microbes in an environment.

While aspects of the present disclosure are described with respect to dispensing a sanitization fluid, it is to be understood that the present disclosure may be applicable to delivering a volume of any fluid to a user's hands and/or other portions of the user's body on an intermittent basis, such as a lotion, medicament, salve, sunscreen, or topical ointment. Additionally, while aspects of the present disclosure are described with respect to dispensing fluid based on an elapsed duration, it should be appreciated that the present disclosure may be applicable to delivering fluid based on one or more other parameters, such as, for example, a temperature, an oxygen level, ambient light exposure, and more.

As used herein, the term "portable" as applied to a device may refer to the device being configured for mobility, e.g., configured to be worn or otherwise carried (e.g., in a user's hand, on an armband, on a wristband, on a clip, in a pocket or bag, on a lanyard, etc.) around, and/or in and out of, an environment. A portable device may generally contain components allowing it to operate freely and independently from the confines of, e.g., a fixed physical source of power, fluid, etc., at least for a period of time.

Reference will now be made to the figures that form a part of the present disclosure.

FIG. 1 depicts, in schematic form, an exemplary system 100 according to aspects of the present disclosure. System 100 may include a network 110, a portable device 120 (also referred to as a portable fluid dispensing device), a base station 130, a sensor 140, a computer system 150, a personal computer 160, and a personal device 170.

System 100 may include various devices, computers, and connective elements in or across one or more locations, configured to interact to achieve one or more aspects of the present disclosure. Each component of system 100 may be located in a single location (e.g., a single building, floor, complex, or geographic area), or may be located in a separate location (e.g., separate buildings, cities, states, provinces, or geographic areas). For example, in some embodiments, base station 130 and sensor 140 may generally be located in a single geographic area, whereas portable device 120 and personal device 170 may travel in and out of the geographic area, and computer system 150 and personal computer 160 may be located in further separated geographic area or areas. Moreover, components of system 100 may be owned or managed by a single entity (e.g., an organization or an individual) or may be managed by multiple entities (e.g., organizations, individuals, service providers, etc.). System 100 may include one or more of each component within system 100 (e.g., multiple portable devices 120, base stations 130, sensors, 140, computer systems 150, personal computers 160, and/or personal devices 170).

Network 110 may be any network configured to connect aspects of system 100. Although network 110 is depicted as being central to system 100, network 110 may include any combination of connections between two or more other components of system 100. Network 110 may include any wired or wireless electronic network, such as a local area network or wide area network (e.g., the internet). In some embodiments, network 110 may include various types of data connections, such as wired connections, fiber optic connections, wireless connections, satellite connections, cellular or other mobile connections, and the like. Network 110 also may include any number of computers, digital storage devices and memory connected via one or more wired or wireless networks. In some embodiments, network 110 may include "cloud" storage.

Portable device 120 (also referred to as a portable fluid dispensing device) is described in further detail elsewhere herein with respect to the exemplary embodiments depicted in FIGS. 2, 3A-3C, 4A, and 4B. Generally, portable device 120 may be configured to hold a predetermined volume of a fluid, such as a sanitization fluid, lotion, or ointment, to be carried (either by hand or by a strap, clip, handle, etc.) by a user, to interact with other components of system 100, to dispense one or more volumes of sanitization fluid to a user, to generate reminders to a user to trigger dispensing of sanitization fluid, and/or to track dispensing of sanitization fluid. In some embodiments, portable device 120 may be sized and configured for ease of portability. For example, a size and shape of portable device 120 may resemble that of a beeper, a mobile phone, or other conventional portable device. In some embodiments, portable device 120 may be configured to adapt a reminder schedule to a particular user, either by "learning" a schedule of a user (e.g., via machine learning or by being provided a specific schedule), and/or to provide reminders to dispense fluid that are tailored to the particular user and/or to particular uses. In some embodiments, portable device 120 may include identifying information (e.g., on an identification chip or other component) that may be used to uniquely identify portable device 120 to other components of system 100. Further, in some embodiments, portable device 120 may be configured to sense its movement, location, proximity to other devices, and/or usage, and to track and store information regarding its use in an internal storage element (e.g., a digital storage drive). In some embodiments, portable device 120 may be configured to send information to, and/or receive information from, another component of system 100, such as base station 130 or computer system 150. As will be described elsewhere herein, portable device 120 may include various components that may work together towards performing one or more of its functions, such as a power source (e.g., a rechargeable or replaceable battery), a processing component, digital storage, one or more components to communicate information via network 110 (e.g., a wired or wireless connection component), a fluid cartridge, one or more triggers, and/or one or more reminder-generating components (e.g., a speaker, a light, a vibrating motor, etc.).

Base station 130 may work in concert with portable device 120 to assist in performing the functions of portable device 120 (e.g., locating portable device 120, providing power to portable device 120, preparing and/or tracking schedules, etc.). To this end, base station 130 may include a power source and a computing/computer storage element. In some embodiments, base station 130 may provide power to portable device 120 via a charging port, charging plate, or other means. In some embodiments, base station 130 may provide a recess, hook, resting place, or other area for placement of portable device 120. In some embodiments, base station 130 may communicate, via a wired or wireless connection (e.g., via network 110), with portable device 120, to track portable device 120, provide portable device 120 with a fluid dispensing reminder schedule (e.g., one or more timings, time intervals, events, or triggers at which to generate fluid dispensing reminders to a user), trigger portable device 120 to generate a fluid dispensing reminder directly (e.g., via a proximity sensor or a wireless signal), and/or collect data stored in portable device 120 regarding usage of portable device 120 (e.g., data regarding locations to which portable device 120 has been taken, volumes of sanitization fluid dispensed from portable device 120, a number and frequency of times that sanitization fluid has been dispensed from portable device 120, etc.). In some embodiments, base station 130 may also communicate with other devices inside and/or out of system 100 (e.g., video tracking devices, electronic medical records systems, etc.) to receive and/or send data that may improve system 100 (e.g., via machine learning, identification of areas for research, or other methods).

In some embodiments, base station 130 may include a computer configured to process data received from portable device 120. For example, base station 130 may include digital storage and/or processing capabilities configured to house algorithms, such as a machine learning algorithm and/or a report generation algorithm, to adapt a fluid dispensing reminder schedule and/or generate reports using data received from portable device 120. In some embodiments, base station 130 may include a user input device and/or a user interface, such that a user or users may interact with base station 130. Users may thus use base station 130 to "check-in" or "check-out" a portable device 120 that is charged at base station 130 or elsewhere, download a fluid dispensing reminder schedule from base station 130 to a portable device 120, update a fluid dispensing reminder schedule stored on a portable device 120, or otherwise interact with components of system 100 or external components. In further embodiments, one or more functions described above with respect to base station 130 may be instead performed on another component of system 100.

In some embodiments, base station 130 may be a device having a plurality functions that are unrelated to portable device 120. For example, in some embodiments, base station 130 may be a mobile phone, personal computer, or other device. In some embodiments, system 100 may include a base station 130 specifically built and configured to interface with one or more portable devices 120. For example, base station 130 may include a mobile device that is communicatively coupled with portable device 120. Base station 130 (e.g., a mobile device) may include a mobile application that is operable to transmit one or more user commands to portable device 120. For example, the one or more user commands may include inputs to change a setting of portable device 120. In some embodiments, base station 130 may transmit one or more user commands to portable device 120 for changing settings of a fluid dispensing volume, a reminder frequency, and more. In other embodiments, system 100 may not include a base station 130 specifically built and configured to interface with portable devices 120; instead, system 100 may include a plurality of devices, computers, etc. that are capable of interfacing with portable devices 120 while also performing other functions (e.g., mobile phones, tablets, etc.) In some embodiments, other components of system 100 may also be able to perform one or more functions of base station 130 (e.g., charge portable device 120, track portable device 120, and/or exchange data with portable device 120).

In some embodiments, base station 130 may be configured to perform any or all of the above functions with respect to multiple portable devices 120. For example, base station 130 may be configured to perform any above function with up to two, up to five, up to ten, up to fifteen, or up to twenty portable devices 120. In some embodiments, base station 130 may be paired (e.g., electronically assigned) to a particular device 120 for a period of time, and may subsequently be paired to another device 120 at another period of time. For example, in an embodiment in which base station 130 is a personal computer or mobile phone of a user, a user may pair a portable device 120 to base station 130 for a period of time while the user uses the portable device 120. The user may subsequently use a different portable device 120, and at that time may pair the different portable device 120 to base station 130.

In some embodiments, "checking in," "checking out," pairing, or otherwise assigning a portable device 120 to base station 130 may include, or may be accomplished by, e.g., establishing a link between the portable device 120 and base station 130, such as a Bluetooth connection or local area network connection. In some embodiments, establishing such a link may be sufficient to allow base station 130 to perform any or all of the above functions with respect to the portable device 120, for at least a period of time. Advantageously, this may allow for multiple portable devices 120 to be used by multiple subsequent users without complex and/or lengthy registration, "check-in," or "check-out" processes.

Sensor 140 may be configured to either sense proximity of portable device 120, or be sensed by portable device 120 when within a particular range of portable device 120. In some embodiments, for example, sensor 140 may be a radio frequency sensor (or any other suitable type of sensor), configured to detect portable device 120 when within a predetermined physical distance of portable device 120. In such embodiments, sensor 140 may include computer circuitry configured to transmit information (e.g., over network 110) to portable device 120 or other components of system 100, indicating that portable device 120 has entered a location particular to sensor 140. In further embodiments, sensor 140 may include a marker (e.g., an RFID chip or other marker) that may be sensed by a sensor within portable device 120 (e.g., proximity sensing module 246 of device 200, described in further detail below) when within the predetermined physical distance of portable device 120. Sensor 140 may thus serve to indicate to portable device 120 that portable device 120 has entered a location shared by sensor 140.

By deliberate placement of one or more sensors 140, sensors 140 may be used to track movement of portable device 120 and/or to identify events to portable device 120 within an environment—e.g., when portable device 120 has entered or left an environment or an area of the environment. By working with sensor 140, portable device 120 may be able to generate location-based reminders to a user of portable device 120. For example, sensor 140 may be placed at an entryway to an area in which regular reminders to use sanitization fluid may be desired (e.g., an entry to an operating room, laboratory, patient quarters, or other area). After a user with portable device 120 enters the area, portable device 120 may begin generating reminders consistent with its location, as determined using sensor 140. After a user with portable device 120 leaves the area, or enters an area in which reminders are not needed (e.g., a recreational area, a personal office, etc.), portable device 120 may likewise stop generating reminders consistent with the area, and/or may begin generating reminders consistent with another area. In some embodiments, sensor 140 may be, or may be a part of, base station 130.

Computer system 150 may be configured to run one or more processes relevant to the usage of, or analysis of data from, personal device 120 and/or base station 130. In some embodiments, one or more of the functions described above with respect to base station 130 may be additionally or alternatively performed by computer system 150. In some embodiments, for example, base station 130 may transmit data regarding portable device 120 to computer system 150 for analysis, storage, and/or generation of reports. For example, base station 130 may include a mobile device having a mobile application configured to perform one or more of the functions described herein. Further, computer system 150 may include a cloud computing system located remotely from base station 130 (e.g., a mobile device) and communicatively coupled to base station 130 via the mobile application. In the example, base station 130 may be operable to transmit and/or receive data from the cloud computing system (e.g., computer system 150) to compute one or more gel dispensing metrics, including, for example, an average gel dispensing activity, an average reminder transmission frequency, an average gel dispensing volume, etc., for one or more users. In some embodiments, computer system 150 may be configured to use data regarding one or more users, one or more institutions, one or more existing schedules, or other data to generate a fluid dispensing reminder schedule for use by portable device 120.

In some embodiments, computer system 150 may house one or more algorithms, such as a machine learning algorithm, configured to be trained or tuned using usage data from one or more portable devices 120. Such an algorithm or algorithms may be used to generate updated fluid dispensing reminder schedules based on existing usage data. In some embodiments, computer system 150 may be configured to compile and process data received from one or more portable devices 120 and/or base stations 130. In some embodiments, for example, computer system 150 may house one or more algorithms for generating reports using received data. In some embodiments, computer system 150 may additionally generate one or more user interfaces for displaying, sending, and/or receiving such reports.

Computer system 150 may be physically located anywhere relative to portable device 120 and/or base station 130. In some embodiments, for example, computer system 150 may be located in the same general location as portable device 120 and/or base station 130. In other embodiments, computer system 150 may be located remotely, e.g., in a different geographic location, from portable device 120 and/or base station 130. In some embodiments, computer system 150 may include multiple computers located in a single or in multiple locations. In some embodiments, computer system 150 may include a cloud computing system.

Personal computer 160 and personal device 170 may be any devices accessible by one or more individuals using system 100 (e.g., users of portable device 120, administrators of system 100, etc.). Personal computer 160 may be any type of computer configured for use by a user, such as a laptop, desktop, or tablet computer. Personal device 170 may likewise be any type of personal portable device, such as, for example, a mobile phone or pager. In some embodiments, personal computer 160 and/or personal device 170 may be configured to perform one or more functions described above with respect to base station 130 and/or computer system 150. Additionally, personal computer 160 and personal device 170 may be configured to display, e.g., reports of usage of portable device 120 generated within system 100. In some embodiments, personal computer 160 and/or personal device 170 may be used by a user of portable device 120.

In some embodiments, aspects of system 100 (e.g., computer system 150, portable device 120, and/or base station 130) may be configured to send and/or receive data to personal computer 160 and/or personal device 170. In some embodiments, such data may be configured for display in a graphical user interface on personal computer 160 and/or personal device 170. In some such embodiments, the graphical user interface may be constructed by a web application (e.g., an interne browser-based user interface) or an application stored on personal computer 160 and/or personal device 170.

In some embodiments, aspects of system 100 (e.g., computer system 150, portable device 120, and/or base station 130) may be configured to receive information from personal computer 160 and/or personal device 170. For example, aspects of system 100 may be configured to receive input data defining and/or altering a fluid dispensing reminder schedule from personal computer 160 and/or personal device 170. As another example, aspects of system 100 may be configured to send data to personal computer 160 and/or personal device 170 regarding dispensing of fluid from portable device 120. Thus, personal computer 170 and/or personal 170 may serve to inform an individual (e.g., a user of portable device 120 or another individual associated with system 100) regarding the programming and use of portable device 120.

Figure 2:
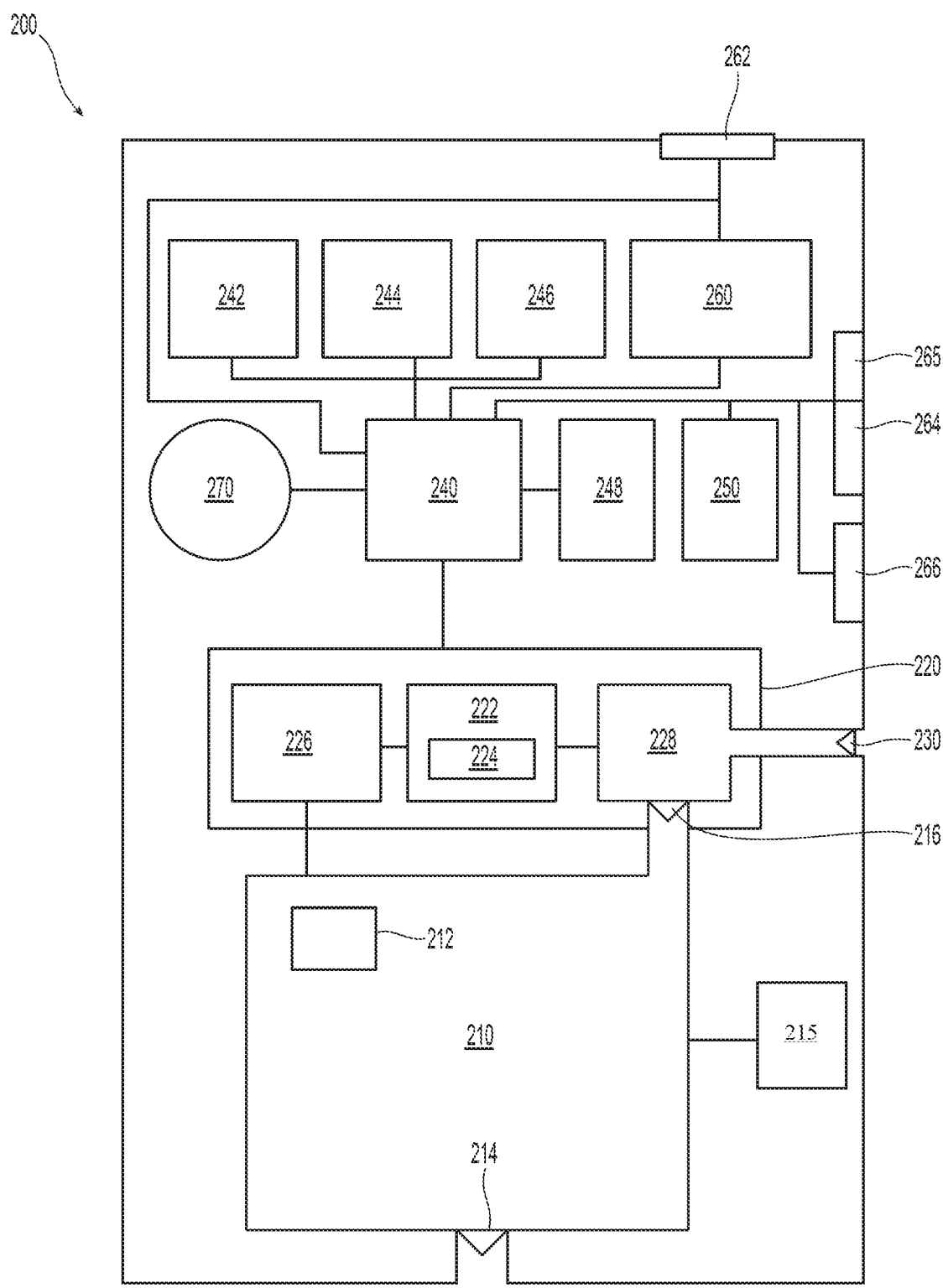
FIG. 2 depicts, in schematic form, exemplary components of a portable fluid dispensing device, according to aspects of the present disclosure.

FIG. 2 depicts, in schematic form, aspects of an exemplary portable device 200 according to aspects of the present disclosure. Device 200 may be an exemplary configuration of portable device 120 of system 100. Device 200 may include a cartridge 210, which may include a cartridge identification chip 212, an outlet valve 214, a pressure release valve 215, and/or an inlet valve 216. Device 200 may further include a pump 220, which may include circuitry 222, a timer 224, a pressure sensor 226, and a pump motor 228 having a pump inlet valve 230. Device 200 may further include processing component 240, a wireless module 242, an accelerometer 244, and a proximity sensing module 246, a device identification chip 248, a vibration module 250, a display 264, a speaker 265, a microphone 266, a tactile trigger 270, a power source 260, and/or a charging port 262.

Aspects of device 200 may be configured to receive information (e.g., user identification information, including one or more user characteristics), interact with an environment in which device 200 is located, aid in reminding a user to dispense an agent (e.g., sanitization fluid or other fluid requiring intermittent use), dispense fluid (e.g., from cartridge 210), and/or collect data regarding reminders and/or fluid dispensing from device 200. Device 200 may have any general size and/or configuration. In some embodiments, device 200 may be portable. For example, device 200 may be able to be carried by hand (e.g., by fitting in a hand or by having a handle), attached to a belt clip, strap, lanyard, or other device, and/or may be able to function independently of an electrical outlet for set periods of time. In some embodiments, device 200 may be configured to be portable at all times except for when charging a power source (e.g., power source 260) or when connected via a wired connection to upload information to and/or download information from other components of a system (e.g., system 100). While aspects of device 200 are described below, it is contemplated that device 200 may have more or fewer than all of the described aspects.

Cartridge 210 may generally include a cavity configured to hold a volume of a sanitization agent, such as a sanitization fluid. In some embodiments, for example, cartridge 210 may be configured to hold a volume of enough fluid such that cartridge 210 (and device 200) may be used intermittently throughout a period of time, such as about 24 hours, about 18 hours, about 12 hours, for the duration of a shift of an occupation or post (e.g., a medical professional's shift at a medical institution), or for the duration of a process or procedure (e.g., a surgical procedure, laboratory procedure, etc.), such as about 6 hours, about 8 hours, or about 10 hours. In some embodiments, cartridge 210 may hold a volume of enough fluid for cartridge 210 (and device 200) to last for a desired period of time assuming that a volume suitable for use is dispensed once about every 10 minutes.

For example, in some embodiments, cartridge 210 may hold a volume of enough fluid to be used about every 10 minutes for about 8 hours, about every 8 minutes for about 6 hours, etc. To that end, cartridge 210 may have any suitable capacity. In some embodiments, cartridge 210 may have a capacity of, e.g., between about 20 mL and about 100 mL, between about 30 mL and about 80 mL, between about 30 mL and about 70 mL, or between about 40 mL and about 60 mL, such as about 30 mL, about 35 mL, about 40 mL, about 45 mL, about 50 mL, about 55 mL, about 60 mL, about 65 mL, about 70 mL, about 75 mL, about 80 mL, about 85 mL, or about 90 mL. Cartridge 210 may also have any other suitable capacity. In some embodiments, other components of device 200 (e.g., pump 220) may be configured to vary a volume of fluid dispensed from cartridge 210 depending on a remaining volume in cartridge 210, as described further below.

Cartridge 210 may be made from any material, such as polymer (e.g., polypropylene). In some embodiments, cartridge 210 may be made from a sterilizable material, a hypoallergenic material, a biocompatible material, a biodegradable material, and/or a recyclable material. In some embodiments, cartridge 210 may include an inner surface configured to discourage adhesion of a fluid within cartridge 210 to the interior of cartridge 210. For example, in some embodiments, cartridge 210 may include a non-stick coating on an inner surface. In other embodiments, cartridge 210 may be manufactured such that an inner surface of cartridge 210 discourages adhesion of fluids to the surface.

In some embodiments, cartridge 210 may be attachable and removable from the rest of device 200 via one or more disengageable attachment mechanisms (e.g., detents, clips, adhesive, extensions, and the like). In other embodiments, cartridge 210 may not be configured to be removed from device 200. In some embodiments, cartridge 210 may be disposable, and in other embodiments, cartridge 210 may be refillable and reusable. In some embodiments, cartridge 210 may be recyclable and/or biodegradable.

In some embodiments, cartridge 210 may include other components, such as cartridge identification chip 212. Cartridge identification chip 212 may include, e.g., electronic circuitry configured to help identify cartridge 210, in the form of, e.g., erasable programmable read-only memory (EPROM) or other read-only memory. In some embodiments, cartridge identification chip 212 may include smart chip technology. Cartridge identification chip 212 may include any type of data that may assist in the identification and/or use of cartridge 210 and/or device 200, such as a manufacturer, a manufacturing lot, a date of manufacture, contents of cartridge 210, ingredients of a fluid within cartridge 210, an expiry date, a seller, compatible devices, and/or a unique identifier. In some embodiments, cartridge identification chip 212 may identify cartridge 210 to another component of device 200 (e.g., circuitry 222 of pump 220, or processing component 240) to ensure compatibility between cartridge 210 and other parts of device 200.

Cartridge 210 may be filled or fillable with any suitable agent. As has been described elsewhere herein, cartridge 210 may be filled with, e.g., a lotion, a medicament, or a sanitization fluid, such as a hand sanitization fluid. Other aspects of cartridge 210 may be adapted to the type of fluid within cartridge 210 (e.g., a capacity of cartridge 210 and/or volume of fluid within cartridge 210 may be selected such that an appropriate volume of fluid is housed within cartridge 210 and/or is dispensed in appropriate volumes). In some embodiments, fluids for use in cartridge 210 may include foaming agents, evaporating agents, and the like.

For example, in some embodiments, cartridge 210 may be filled or fillable with a hand sanitization fluid having ethanol, such as about 70% ethanol. In some embodiments, a hand sanitization fluid for use in cartridge 210 may include a higher-than-average concentration of a disinfecting or antimicrobial agent, such that a smaller volume of fluid may be used to achieve a desired level of sanitization. For example, in some embodiments, a hand sanitization fluid may include antimicrobial agents, such as chlorhexidine gluconate (CHG).

Outlet valve 214 of cartridge 210 may be a valve configured to allow dispensing of fluid from cartridge 210. To this end, outlet valve 214 may be any suitable type of valve. In some embodiments, outlet valve 214 may be, e.g., an x-slit valve and/or a pressure-sensitive valve. For example, outlet valve 214 may open at a fixed threshold opening pressure and may close at a fixed threshold closing pressure. In some embodiments, cartridge 210 may be fillable via an opening where outlet valve 214 is intended to be located, after which the opening may be covered or closed using outlet valve 214.

Inlet valve 216 may allow for pressure from a pump (e.g., pump 220) to enter cartridge 210. In some embodiments, inlet valve 216 may be opened (e.g., punctured or otherwise pushed open) when cartridge 210 is assembled to the remainder of device 200. Inlet valve 216 may form a closed fluid connection with an outlet of pump 220 (e.g., from pump motor 228), such that pressure from pump 220 may reliably be applied to an interior of cartridge 210. In some embodiments, device 200 may include pressure release valve 215 in communication with cartridge 210. Pressure release valve 215 may be configured to control a pressure generated within the interior of cartridge 210 after a dispensing event, such as, for example, by pump 220. By way of example, pressure release valve 215 may include a solenoid operable to supply power (e.g., an electric field, a voltage, etc.) to cartridge 210 to reduce the pressure built therein by pump 220 after the dispensing event. In some embodiments, the solenoid may be operable to activate automatically in response to the occurrence of the dispensing event (e.g., actuation of pump 220) to return the interior of cartridge 210 to atmospheric pressure. It should be appreciated that controlling a pressure of the interior of cartridge 210 (e.g., at and/or near atmospheric levels) may inhibit inadvertent dispensing activities of fluid from cartridge 210 due to built-up pressure within cartridge 210 and physical movement of device 200.

Pump 220 may be any suitable pump sized and configured to fit within device 200 and to pump a specific volume or specific volumes of fluid out of cartridge 210 via outlet valve 214. In some embodiments, for example, pump 220 may be a pressure-sensitive pump. In some embodiments, pump 220 may be configured to provide, e.g., air pressure, physical pressure, or other type of force to cartridge 210. Pump 220 may, in some embodiments, be an electronic or electromechanical pump including one or more of circuitry 222, timer 224, pressure sensor 226, and pump motor 228 with pump inlet valve 230.

Circuitry 222 of pump 220 may control aspects of pump 220 (e.g., timer 224, pressure sensor 226, and/or pump motor 228) and/or may allow pump 220 to be programmable. For example, circuitry 222 may be programmed or instructed to control aspects of pump 220 such that a specific predetermined volume of fluid (e.g., 0.8 mL, 1 mL, 1.2 mL, etc.) is dispensed from cartridge 210 each time pump 220 is activated, or such that a variable volume of fluid (e.g., 0.8 mL, 1.2 mL, etc.) dispensed from cartridge 210 depends on a type of signal received from, e.g., processing component 240. For example, a first signal received from processing component 240 may indicate that a first volume of fluid (e.g., 0.8 mL) should be dispensed from cartridge 210, a second signal may indicate that a second volume of fluid (e.g., 1.2 mL) should be dispensed from cartridge 210, and so on. As another example, pump 220 may be programmed, via circuitry 222, to track a volume of fluid within cartridge 210 (e.g., via tracking an initial volume of cartridge 210 and a number of times and durations for which pump motor 228 has been active). Circuitry 222 may adjust a duration for which pump 220 is kept active to dispense a predetermined volume of fluid from cartridge 210, depending on a volume of fluid within cartridge 210. In some embodiments, circuitry 222 may use data received from, e.g., timer 224 and/or pressure sensor 226 to determine a remaining volume of fluid within cartridge 210, to determine how long pump motor 228 should be active, and/or to determine a volume of fluid that should be dispensed per activation of pump motor 228. Thus, pump 220 advantageously may be capable of dispensing a predetermined or desired volume of fluid from cartridge 210, independent of a remaining volume of fluid within cartridge 210. Additionally, pump 220 may be capable of dispensing a precise and/or adjustable volume of fluid from cartridge 210 (e.g., with a variability of 10% or less), as compared to a mechanical pump (which may have, e.g., a greater variability, such as about 30%). In some embodiments, circuitry 222 may be configured to output a signal, e.g., to processing component 240 or another component of device 200 (e.g., display 264) when circuitry 222 has calculated that cartridge 210 is empty or is nearing empty.

In further embodiments, circuitry 222 may receive instructions from, e.g., processing component 240 to operate components of pump 220 such that a particular volume of fluid is dispensed from cartridge 210. For example, in some embodiments, processing component 240 may receive an input indicating that a specific volume of fluid should be dispensed from cartridge 210 (e.g., a particular trigger, a timed input, or a combination of a particular trigger at a given time interval, etc.), and may instruct circuitry 222 to operate pump 220 such that the specific volume of fluid is dispensed.

Timer 224 may be connected to, or may be a component of, circuitry 222, that may allow for circuitry to time certain events, such as a time for which pump motor 228 is active. Pressure sensor 226 may likewise be connected to circuitry 222 and may be used to sense a pressure in cartridge 210 during use of device 200. Pressure sensor 226 may include any suitable pressure sensing apparatus and/or technology. By receiving a pressure that is sensed in cartridge 210 from pressure sensor 226, circuitry 222 may modulate a time for which pump motor 228 is active and/or a volume of pressure supplied to cartridge 210 via pump motor 228 to ensure that a desired volume of fluid is dispensed from cartridge 210 during an operation of pump motor 228.

Pump motor 228 may be any suitable type of pump motor configured to supply pressure to cartridge 210. For example, in some embodiments, pump motor 228 may be an air pressure pump motor. Pump motor 228 may be controlled by circuitry 222 to supply pressure to cartridge 210 via inlet valve 216. Specifically, pump motor 228 may move air into device 220 from pump inlet valve 230 and into cartridge 210 via inlet valve 216, until the pressure in cartridge 210 is sufficient to open outlet valve 214 (e.g., as sensed by pressure sensor 226). Pump motor 228 may continue to supply a specific pressure to cartridge 210 for a specific period of time after outlet valve 214 is opened, to ensure that a desired volume of fluid is dispensed from cartridge 210.

Processing component 240 may include any suitable electronic circuitry configured to control various aspects of device 200. In some embodiments, processing component 240 may include a central processing unit (CPU), digital storage (e.g., a solid state drive) and/or other components. Generally, processing component 240 may indirectly or directly receive information from any component of device 200, may process received information, and/or may send information (e.g., instructions) to any component of device 200. Processing component 240 may be programmed by, e.g., external data received by any means (e.g., via wireless module 242, accelerometer 244, and/or charging port 262). In some embodiments, processing component 240 may be programmed prior to assembly within device 200. For example, a series of instructions, a fluid dispensing reminder schedule, instructions for tracking and/or recording dispensing of fluid, or other data may be programmed onto processing component 240. Using the received programming and/or instructions, processing component 240 may coordinate any and/or all functions of device 200. For example, processing component 240 may be configured to receive a trigger from, e.g., accelerometer 244, wireless module 242, accelerometer 244, proximity sensing module 246, microphone 266, and/or tactile trigger 270. Depending on the trigger received, processing component 240 may instruct pump 220 to activate, in order to dispense a specific volume of fluid from cartridge 210.

In some embodiments, processing component 240 may be configured to process a type of trigger received from one or more other components of device 200. For example, processing component 240 may be configured to process voice commands received via speaker 26, a number of taps or other inputs from tactile trigger 270, and/or a type of movement from accelerometer 244. As a further example, processing component 240 may be configured to receive data from proximity sensing module regarding proximity to another type of device (e.g., base station 130 or sensor 140 of system 100). Based on the processed trigger or data, processing component 240 may be configured to implement, adjust, start, or stop a fluid dispensing reminder schedule, and/or to activate pump 220 and dispense an appropriate volume of fluid from cartridge 210. The fluid dispensing reminder schedule may include outputting reminders to one or more components of device 200, such as display 264, vibration module 244, and/or speaker 265.

In some embodiments, processing component 240 may be configured to adapt to use of device 200 over a period of time. For example, at a predetermined time of day, processing component 240 may send instructions to one or more components of device 200 (e.g., to speaker 265, display 264, and/or vibration module 244) to output a reminder (e.g., in the form of an auditory reminder, a visual reminder, and/or a vibration reminder). Processing component 240 may then wait a predetermined amount of time for a trigger indicating that fluid should be dispensed from cartridge 210 (e.g., a trigger from microphone 266 and/or tactile trigger 270). If no trigger is received, then processing component 240 may adapt such that, at the predetermined time of day, processing component 240 does not send instructions to the one or more components of device 200 to output a reminder. In some embodiments, processing component 240 may collect data as to whether output reminders are and/or are not followed by a received trigger to dispense a volume of fluid during certain times of day over a period of multiple days, before adapting a reminder schedule to output, or not output, reminders during those times of day. Additionally and/or alternatively, processing component 240 may likewise collect data as to whether certain cues received from components of device 200 (e.g., proximity to an external device detected by proximity sensing module 246), in response to which reminders are output, are followed by a received trigger to dispense a volume of fluid.

In a similar manner, processing component 240 may be involved in controlling device 200 and/or collecting data at device 200 as a part of any process, method, or system (e.g., system 100) including device 200.

Wireless communication module 242 may be any suitable component of device 200 providing wireless connection capabilities to, e.g., processing component 240 and/or other components of device 200. In some embodiments, for example, wireless communication module 242 may include a wireless card configured to allow components of device 200 to connect to a wireless network (e.g., a local area network or wide-area network, such as the internet). In some embodiments, wireless communication module 242 may include Bluetooth connection capabilities (e.g., a Bluetooth adapter) and/or other wireless communication capabilities.

Generally, wireless communication module 242 may allow for wireless communication between device 200 and any other suitable device in a system of which device 200 is part (e.g., base station 130, computer system 150, personal computer 160, and/or personal device 170 of system 100). Components of device 200 (e.g., processing component 240 and/or circuitry 222) may send and/or receive instructions, programming, algorithms, and/or updates over wireless communication module 242.

Accelerometer 244 may be configured to receive and transmit to processing component 240 various types of movement of device 200, such as movements corresponding to walking or shaking of device 200. In some embodiments, accelerometer 244 may further be configured to transmit to processing component 240 notification of a lack of movement (i.e., stillness) of device 200. Movement (or lack thereof) detected by accelerometer 244 may be used to, e.g., trigger dispensing of a volume of fluid from device 200 (e.g., by shaking device 200), determine a location of device 200, and/or determine whether device 200 is in use (e.g., by detecting movement) or not (e.g., by detecting stillness).

Proximity sensing module 246 may be configured to receive and transmit to processing component 240 signals dependent on the proximity of another device (e.g., another component of system 100) to device 200. For example, proximity sensing module 246 may include radio frequency sensing technology, digital sensing technology, or other types of sensing technology configured to sense proximity of device 200 to other devices and/or locations. In some embodiments, proximity sensing module 246 (optionally in conjunction with processing component 240) may be configured to sense and distinguish various different types of devices and/or locations, so as to more specifically identify a location of device 200 in relation to other devices and/or locations. Moreover, aspects of a system including device 200 (e.g., system 100) may be equipped, labeled, tagged, etc. with identification circuitry, chips, or other technology configured to be sensed and identified by proximity sensing module 246 (optionally with processing component 240). Furthermore, different aspects (e.g., components) of a system may be equipped to be detected by device 200 when device 200 is at different ranges from them. For example, a first sensor (e.g., sensor 140) may be detectable by device 200 when device 200 is within, e.g., ten feet of it, and a second sensor may be detectable by device 200 when device 200 is within, e.g., five inches from it. These ranges are merely exemplary, and any suitable range may be employed.

Thus, using proximity sensing module 246, processing component 240 may be programmed to perform one or more given functions, such as generating a fluid dispensing reminder, starting a fluid dispensing reminder schedule, stopping a fluid dispensing reminder schedule, or instructing pump 220 to dispense a volume of fluid from device 200, when in proximity to another device. For example, proximity sensing module 246 may be configured to sense proximity to a labeled location, such as an entryway or exit to a particular environment (e.g., a medical facility, hospital, laboratory, etc.). Based on receiving this information, processing component 240 may be configured to start and/or stop outputting fluid dispensing reminders from device 200. As another example, proximity sensing module 246 may be configured to sense proximity to a triggering device in a particular room, such as a triggering sensor on an operating room or laboratory bench. Based on receiving this information, processing component 240 may be configured to instruct pump 220 to dispense a predetermined volume of fluid from cartridge 210 of device 200.

Device identification chip 248 may be any type of chip containing identifying information for device 200. In some embodiments, for example, device identification chip 248 may be a microchip, such as a chip containing EPROM or radio frequency identification (RFID) technology, or may be any other suitable type of chip configured to carry identifying information for device 200. Device identification chip 248 may be configured to be read by other components of a system containing device 200 (e.g., base station 130, computer system 150, sensor 140, etc.).

In some embodiments, device identification chip 248 may include data identifying device 200 (e.g., with an identification number or other tag) a user of device 200, a manufacturer of device 200, one or more types of cartridge 210 compatible with device 200, or any other identifying information. Device identification chip 248 may be of use in tracking, e.g., a location of device 200, use of device 200, or other information about device 200. In some embodiments, such information may be used to, e.g., generate reports as to the location and/or use of device 200 over time. In particular, device identification chip 248 may be of use in systems containing many devices 200, so as to distinguish devices from one another.

Vibration module 250 may include, e.g., a vibration motor or vibration-causing component, configured to cause device 200 to vibrate when activated. For example, vibration module 250 may include an eccentric rotating mass vibration motor or a linear resonant actuator vibration motor, or any other suitable type of vibration-causing component. Processing component 240 may work in conjunction with vibration module 250 to, e.g., cause device 200 to vibrate at desired times. For example, if processing component 240 determines that a fluid dispensing reminder should be generated, it may activate vibration module 250 to cause device 200 to vibrate, which may serve as the fluid dispensing reminder. Moreover, processing component 240 may cause vibration module 250 to generate different vibration durations and/or patterns to convey different types of messages and/or alerts to a user of device 200. For example, a first vibration pattern or duration may correspond to a fluid dispensing reminder. A second vibration pattern or duration may correspond to a notification that the power source of device 200 (e.g., power source 260) is low on power. Similarly, other messages and/or alerts may correspond to further vibration patterns and/or durations.

Display 264 may be any type of display configured to convey messages and/or alerts to a user of device 200. In some embodiments, display 264 may include one or more simple lights, such as light-emitting diodes (LEDs). In further embodiments, display 264 may include one or more lights overlaid with a pattern of symbols corresponding to different messages and/or alerts (e.g., a symbol showing a battery, a wireless connectivity symbol, a symbol showing an empty cartridge, etc.). Each symbol may be lit up when relevant to convey a related message to a user (e.g., a level of power remaining in power source 260 (see, e.g., charge indicator 356 of device 300), an indicator that device 200 is wirelessly connected to other devices via a network, or that cartridge 210 is near depleted). In further embodiments, display 264 may include a digital screen configured to display different images, text, numbers, and/or alerts. Processing component 240 may work in conjunction with display 264 to convey various types of information to an individual via device 200.

Speaker 265 and microphone 266 may include either a separate speaker and microphone, or may include a combined speaker and microphone configured to output auditory cues to, and receive auditory cues from, an environment in which device 200 is located. In some embodiments, for example, microphone 266 may receive an auditory cue (e.g., a voice command or other cue) which processing component 240 may interpret as requiring a response (e.g., dispensing a volume of fluid corresponding to the cue). In some embodiments, for example, processing component 240 may distinguish multiple different auditory cues to each correspond to a different volume of fluid that should be dispensed from device 200 in response. Moreover, speaker 265 may output, e.g., fluid dispensing reminders (e.g., chimes, beeps, ringing sounds, or other noises) to a user of device 200. Additionally or alternatively, speaker 265 may output, e.g., an alert when power source 260 is low on power, when proximity sensing module 246 indicates that device 200 is entering, exiting, or nearing a notable location (e.g., entering or exiting an area in which fluid dispensing reminders will be generated, nearing a base station (e.g., base station 130), or nearing a component of a system (e.g., system 100) with which device 200 may otherwise interact.

Each of vibration module 250, display 264, and speaker 265 may be used, e.g., by processing component 240, in any way to convey messages, alerts, or information to individuals in an environment with device 200. While examples are described above, one of ordinary skill in the art will understand that many additional types of messages, alerts, and/or information may be conveyed using these components of device 200.

Tactile trigger 270 may be any type of input component that may convey a signal to other components of device 200 (e.g., processing component 240 and/or pump 220) when triggered by physical touch. In some embodiments, for example, tactile trigger 270 may include a mechanical button, capacitive touch sensor, switch, etc. In some embodiments, tactile trigger 270 may be configured to be activated, engaged, etc. only when touched, pressed, switched, etc. in a particular pattern (e.g., a specific number of touches, presses, switches, etc. in a given period of time) to prevent accidental engagement of tactile trigger 270. In some embodiments, tactile trigger 270 may be configured to be activated, engaged, etc. by the use of a single hand that is also positioned at an opening of cartridge 210, so as to be easily usable by one hand.

Power source 260 may be any type of power source for storing and supplying a portable source of power to components of device 200. In some embodiments, for example, power source 260 may be a rechargeable battery. Charging port 262 may be a port in which a wired connection may be established to device 200 from another component of a system of which device 200 is a part (e.g., computer system 150, base station 130, personal device 170, personal computer 160, or other component). Charging port 262 may be configured to supply power to power source 260 and/or directly to other components of device 200. Moreover, charging port 262 may double as a port for a wired data connection to device 200 from other devices. Thus, charging port 262 may be used to supply data (e.g., instructions) to, e.g., processing component 240, download data from processing component 240, and/or otherwise interact with processing component 240 or other components of device 200.

Figure 3B:
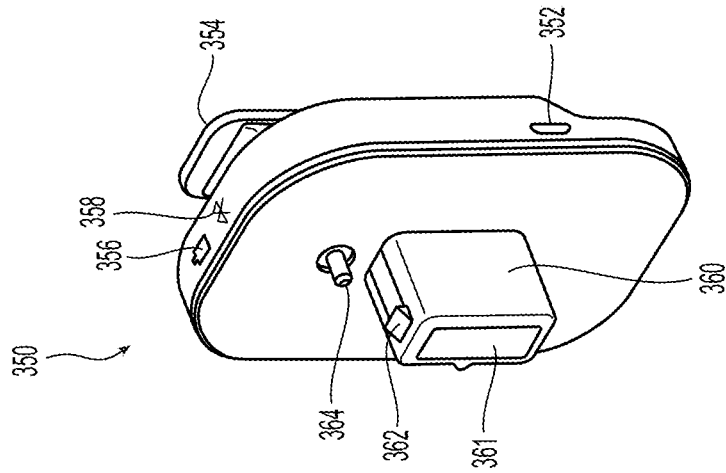
FIGS. 3A-3C depict views of an exemplary portable fluid dispensing device, according to aspects of the present disclosure.
Figure 3A:
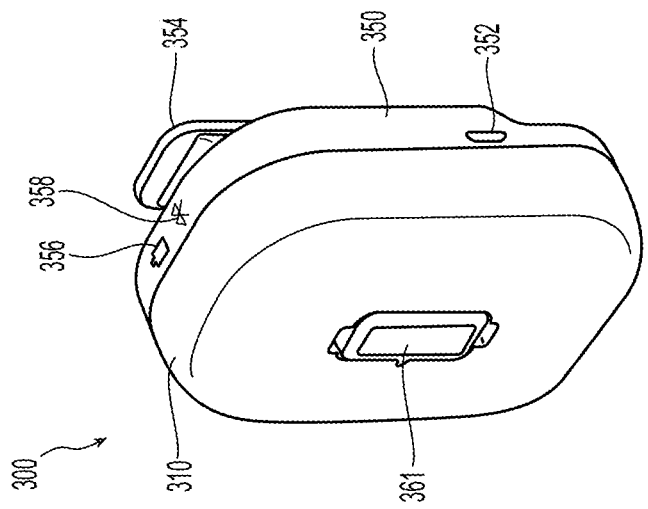
Figure 3C:
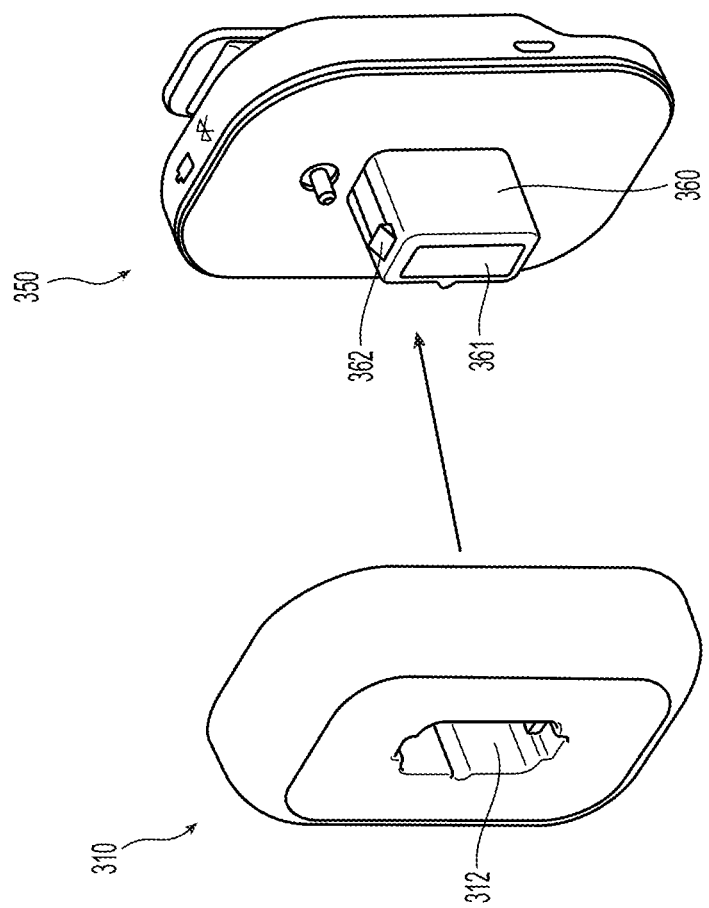

FIGS. 3A-3C depict an exemplary portable device 300, which may be a specific configuration of device 200, according to the present disclosure. FIG. 3A depicts device 300 in an assembled configuration including a cartridge 310 and a housing 350, while FIG. 3B depicts housing 350 separately.

As shown in FIG. 3A, device 300 may include cartridge 310 and housing 350. Housing 350 includes a charging port 352, a clip 354, a charge indicator 356, a connectivity indicator 358, and a connection piece 360. As shown in FIG. 3B, connection piece 360 may include a detent 362. Housing 350 may further include a pump outlet 364.

Figure 4B:
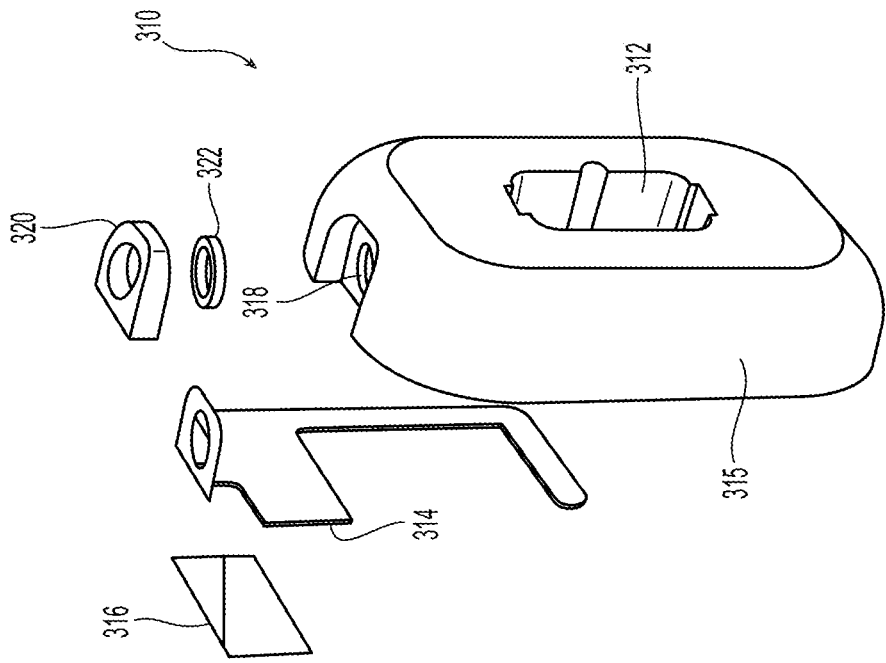
FIGS. 4A and 4B depict views of an exemplary portable fluid dispensing device cartridge, according to aspects of the present disclosure.

Cartridge 310 may share any characteristics with, e.g., cartridge 210, and is described in further detail below with respect to FIGS. 4A and 4B. Housing 350 may contain remaining components of device 300, some of which may correspond to components of device 200. For example, charging port 352 may share any characteristics with charging port 262. Charge indicator 356 and connectivity indicator 358 may be a part of a display (e.g., display 264). Specifically, charge indicator 356 may indicate a level of charge remaining in a power source of device 300, and connectivity indicator 358, when lit, may indicate that device 300 is actively wirelessly connected to another device (e.g., via a Bluetooth connection). Although not depicted, device 300 may additionally or alternatively include one or more other types of indicators as a part of a display.

Clip 354 may be used to detachably affix device 300 to another item, such as an item of clothing of a user of device 300. In some embodiments, clip 354 may be replaceable with a lanyard, strap, or other device. Connection piece 360 may be configured to physically interact with cartridge 310, to connect cartridge 310 to housing 350.

Pump outlet 364 may be configured to interact with an opening (not shown) of cartridge 310 when cartridge 310 is assembled together with housing 350. When cartridge 310 is assembled together with housing 350, an opening of pump outlet 364 may be situated inside cartridge 310, such that a pump of housing 350 may provide pressure to an interior of cartridge 310 and cause fluid to be dispensed from an opening (e.g., opening 318, depicted in FIG. 4B) of cartridge 310.

FIG. 3C depicts a process of assembling cartridge 310 to housing 350. Cartridge 310 may include an opening 312 configured to accept connection piece 360. An interior geometry of opening 312 (not shown) may be configured to interface with detent 362 of housing 350, such that once connection piece 360 is accepted into opening 312, detent 362 prevents detachment of cartridge 310 from housing 350 until detent 362 is released. Detent 362 may be released by an internal mechanical mechanism (not shown) of connection piece 360. Such an internal mechanical mechanism may be activated by, e.g., pressing a front portion 361 of connection piece 360, which may be accessible through opening 312.

Figure 4A:
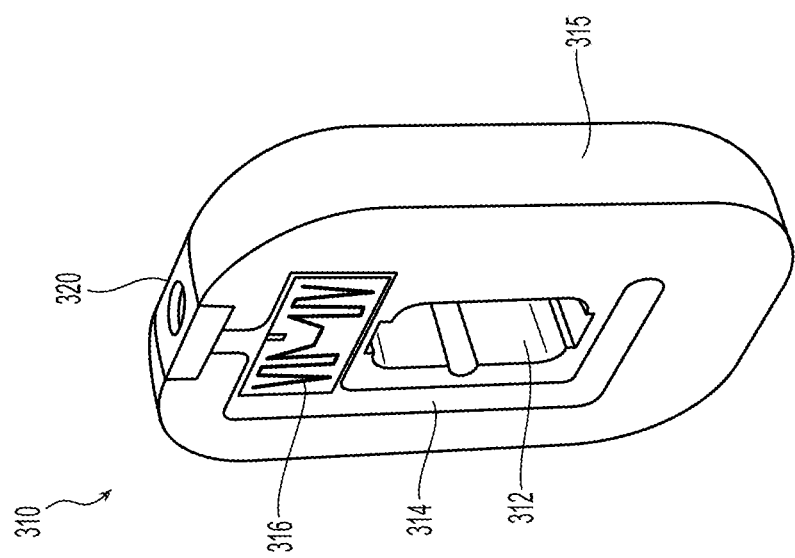

FIG. 4A depicts an additional view of cartridge 310. Cartridge 310 includes a body 315, a valve cover 320, an adhesive strip 314, an identification chip 316, and opening 312. As shown in the exploded view of FIG. 4B, a valve 322 is positioned between an opening 318 into body 315 and valve cover 320.

As previously stated, cartridge 310 may share any characteristics with cartridge 210 of device 200. For example, body 315 of cartridge 310 may be made from polypropylene, and may include an inner coating (not shown) to prevent fluid from adhering to an interior of cartridge 310. In some embodiments, cartridge 310 may be disposable, biodegradable, and/or recyclable. An adhesive strip 314 may be applied to a surface of cartridge 310 to adhere identification chip 316 to the surface of cartridge 310. Identification chip 316 may share any characteristics with, e.g., cartridge identification chip 212 of device 200. In some embodiments, identification chip 316 may be removable from cartridge 310, e.g., after cartridge 310 has been used. This may allow for added recyclability of cartridge 310 and/or identification chip 316.

Valve 322 may share any characteristics with, e.g., outlet valve 214 of device 200. For example, valve 322 may be an x-slit pressure-sensitive valve, which may open at a fixed threshold opening pressure and may close at a fixed threshold closing pressure. Valve cover 320 may be, e.g., a piece configured to hold valve 322 in place over opening 318 of cartridge 310. In some embodiments, valve cover 320 may be configured for assembly to body 315 of cartridge 310 via, e.g., a snap fit connection, a sliding fit connection, or other mode of assembly that may reduce or prevent accidental removal or detachment of valve cover 320. In some embodiments, valve cover 320 may be affixed to body 315 by, e.g., an adhesive, such as a glue. Opening 318 may allow ingress and egress of fluid to and from an interior of cartridge 310.

While aspects of device 300 have been described above, it is to be understood that device 300 may have any additional or alternative components that have been described with respect to device 200.

Reference will now be made to exemplary versions of a method of using the portable devices described according to aspects of the present disclosure. The versions of a method described herein serve to highlight additional features, capabilities, and variations of portable devices according to the present disclosure, as well as systems in which they may be used. Any such additional features, capabilities, and variations may be combined and/or included in the systems and devices that have been described herein (e.g., system 100, device 200, and/or device 300).

Figure 5:
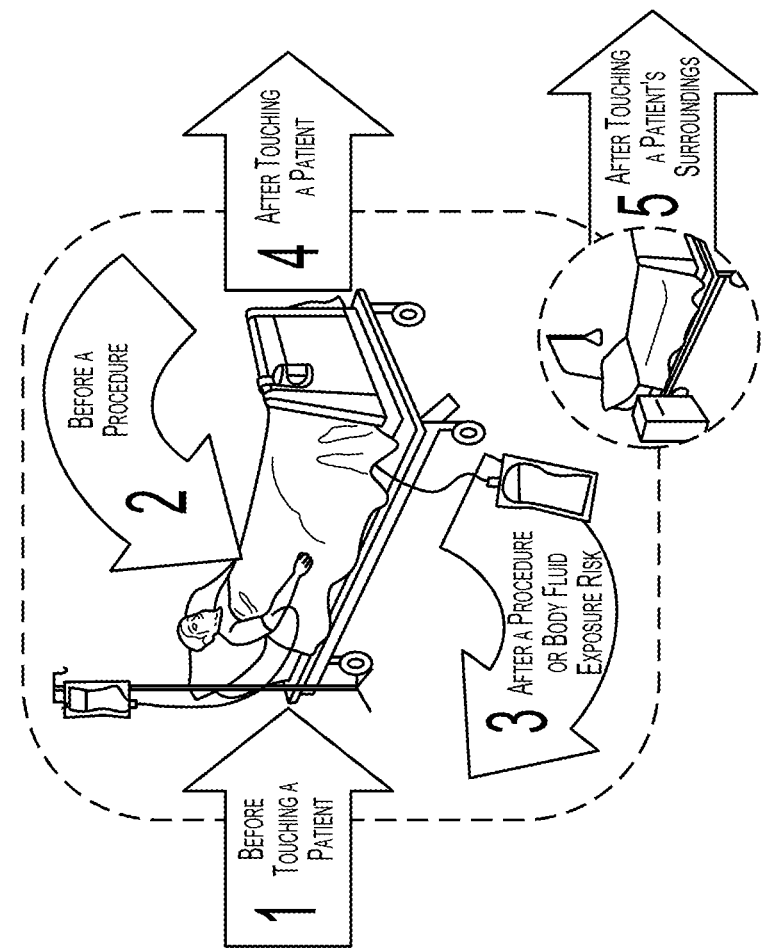
FIG. 5 depicts an exemplary series of sanitization reminders, according to aspects of the present disclosure.

Devices and systems of the present disclosure may be applicable in a variety of environments, such as environments within medical facilities (e.g., hospitals, doctor's offices, surgical centers, pharmaceutical centers, etc.), laboratories (e.g., research laboratories, diagnostic laboratories, experimental laboratories, pharmaceutical laboratories, etc.), food or drug preparation environments (e.g., manufacturing centers, factories, packaging environments, etc.), or other environments. In some cases, devices and systems of the present disclosure may be applicable in temporary or moving environments, such as in areas where medical assistance or laboratory services are being provided temporarily (e.g., field medicine, first aid camps, medic trailers, blood drive trailers, etc.). In particular, environments in which medical care is being offered may be suited to devices and systems of the present disclosure, because such environments are often subject to regimented standards of care and cleanliness. For example, the World Health Organization provides an approach for hand hygiene called "My 5 Moments of Hand Hygiene." A depiction of this approach is provided in FIG. 5, which shows five times at which health-care workers should clean their hands: (1) before touching a patient; (2) before clean/aseptic procedures; (3) after body fluid exposure/risk; (4) after touching a patient; and (5) after touching patient surroundings. Other similar types of systems may also provide guidelines to health-care workers. Devices, systems, and methods of the present disclosure may be particularly helpful in helping adherence to such guidelines.

Figure 6:
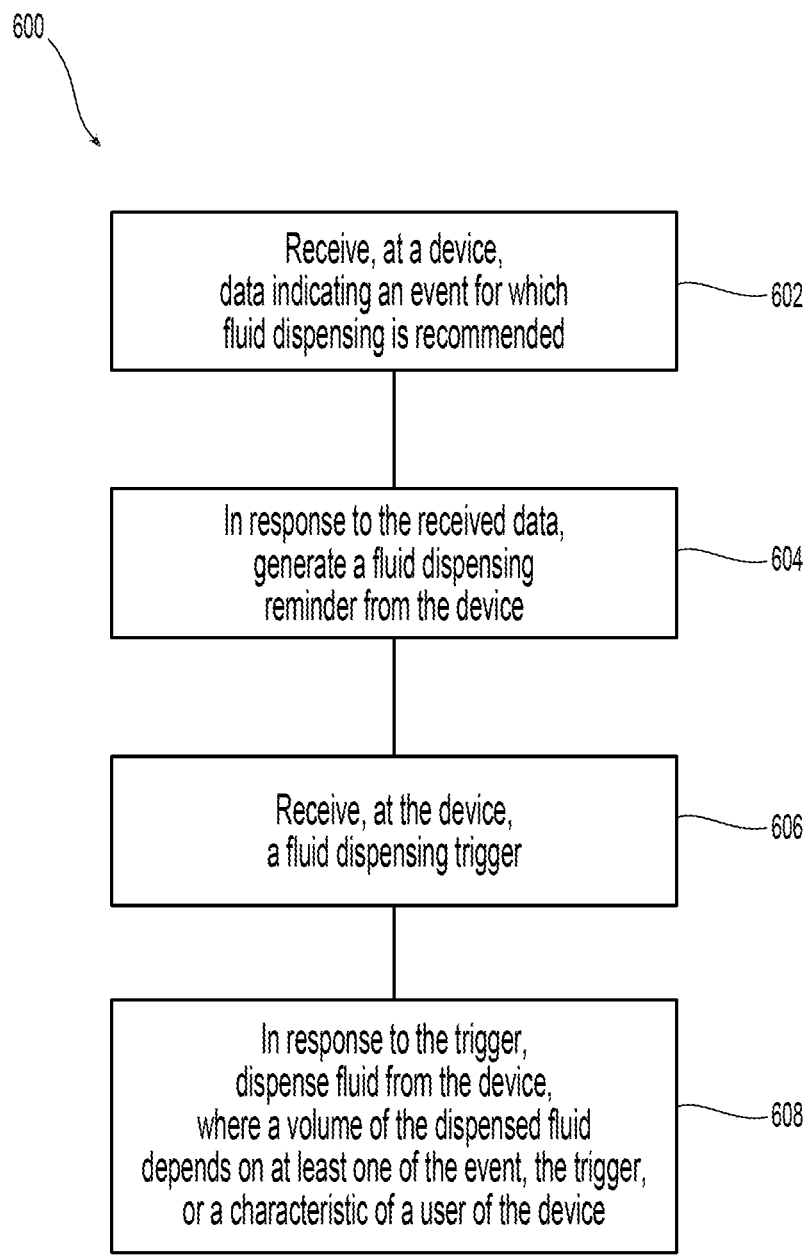
FIG. 6 depicts, in flow chart form, a method of generating reminders for dispensing of a fluid from a device, according to aspects of the present disclosure.

FIG. 6 depicts, in flow chart form, a method 600 of generating reminders for dispensing of a fluid from a device, according to aspects of the present disclosure. Method 600 may be performed by a portable device (e.g., devices 120, 200, 300), in combination with other components of a system including the portable device. According to step 602, data may be received, indicating an event for which dispensing of fluid is recommended. As has been discussed with respect to devices 200 and 300 herein, data indicating an event for which dispensing of fluid is recommended may be received at a portable fluid dispensing device from any of various sources. In some embodiments, for example, data may be generated and received at a processing component (e.g., processing component 240 of device 200) indicating that a certain amount of time has lapsed since a previous dispensing of fluid, and that another dispensing of fluid is therefore recommended. In some embodiments, a processing component (e.g., processing component 240 of device 200) may be programmed with a schedule of reminders, and a timer of the processing component may indicate that a time for a reminder on the schedule of reminders has arrived. In some embodiments, data may be received from an external source, such as a sensor (e.g., sensor 140 of system 100), and/or may be received at, e.g., a proximity sensor of a device (e.g., proximity sensing module 246 of device 200), indicating that the device has reached a location at which a fluid dispensing reminder is appropriate or needed. For example, data may be received from base station 130 (e.g., a mobile device) when base station 130 receives a beacon signal from an external system indicative of a fluid dispensing reminder. The mobile device may include a mobile application that is configured to receive (e.g., via Bluetooth) the beacon signal from an external system positioned at one or more target areas, such as, for example, an entranceway, an exit, a room, and more. In this instance, the mobile application may transmit a smart reminder to the user's attention for dispensing fluid based on a current location of the mobile device relative to the one or more target areas.

In further embodiments, a frequency in which fluid dispensing reminders are generated may be modified based on a current geolocation of base station 130 (e.g., detected by a sensor internal to base station 130). For example, base station 130 may include a mobile device with a mobile application that is configured to determine a sensed position or location of the mobile device (e.g., by geofencing, GPS beacon tracking, Bluetooth, etc.) and automatically adjust a frequency setting of the fluid dispending reminders based on the current geolocation of the mobile device. By way of illustrative example, the mobile application may be operable to increase the frequency setting of the fluid dispensing reminders when the mobile device is located within high-risk areas (e.g., public venues, hospitals, grocery stores, gas stations, parks, etc.) and/or decrease the frequency setting when the mobile device is located within low-risk areas (e.g., a residence, a vehicle, an office, etc.).

According to step 604, a fluid dispensing reminder may be generated from the device. As has been discussed with respect to device 200 herein, a fluid dispensing reminder may be auditory (e.g., from speaker 265 of device 200), visual (e.g., from display 264 of device 200), or physical (e.g., a vibration from vibration module 250 of device 200).

According to step 606, a fluid dispensing trigger may be received at the device. In some embodiments, the fluid dispensing trigger may be in response to a user noticing the fluid dispensing reminder. The fluid dispensing trigger may be received as an input from any part of the device configured to allow for such input—for example, the fluid dispensing trigger may be a tactile cue (e.g., received as one or more taps, presses, or other cues from tactile trigger 270 of device 200), a motion cue (e.g., received as motion input from, e.g., accelerometer of device 200), or an auditory cue (e.g., received as input, such as voice input, from microphone 266 of device 200).

According to step 608, a volume of fluid may be dispensed from the device, where the volume of dispensed fluid depends on at least one of the event, the trigger, or a characteristic of a user of the device. In some embodiments, for example, a fluid dispensing reminder schedule may include, as a part of the schedule, an indicated predetermined volume of fluid to dispense from the device. In further embodiments, a volume of fluid dispensed from the device may depend on an amount of time since fluid was last dispensed from the device. For example, in some embodiments, a first volume may be dispensed if the amount of time lapsed since fluid was previously dispensed is greater than a threshold, and a second volume may be dispensed if the amount of time lapsed since fluid was previously dispensed is less than or equal to the threshold. As a further example, a first volume may be dispensed if the amount of time lapsed since the last time fluid was dispensed is greater than a first threshold. A second volume may be dispensed if the amount of time lapsed since the last time fluid was dispensed is less than the first threshold, but greater than a second threshold. A third volume may be dispensed if the amount of time lapsed since the last time fluid was dispensed is less than the second threshold. For example, in one embodiment, a minimum recommended volume of sanitization fluid to be dispensed may be, e.g., 1.2 mL if more than 30 minutes have lapsed since the last time fluid was dispensed from the device. A minimum recommended volume of 1.0 mL may be dispensed if more than 5 minutes, but 30 minutes or fewer, have lapsed since the last time fluid was dispensed from the device. And, a minimum recommended volume of 0.8 mL may be dispensed if 5 minutes or fewer have lapsed since the last time fluid was dispensed from the device. These recommended volumes and time thresholds are exemplary, and many more combinations of recommended volumes and time thresholds are contemplated herein. For example, specific minimum recommended volumes may depend on, e.g., a type of fluid within the device, a desired effect of the fluid a characteristic of the user (e.g., user hand size), etc.

In still further embodiments, a sensed position or location of the device (e.g., detected by a sensor external to the device (e.g., sensor 140 of system 100) or by a proximity sensing module within the device (e.g., proximity sensing module 246 of device 200)), may influence the volume of fluid to be dispensed from the device. In other embodiments, a sensed position or location of base station 130 (e.g., a mobile device) may influence the volume of fluid to be dispensed from the device. In some embodiments, for example, a high-risk area may be identified based on the sensed location of the device and/or base station 130 (e.g., via geofencing, GPS beacon tracking, Bluetooth, etc.), in which a higher volume of sanitization fluid than average may be dispensed by the device when the device is sensed as being in that area. By way of further example, a low-risk area may be identified in which a lower volume of sanitization fluid than average may be dispensed by the device when the device is sensed as being in that area. In further embodiments, a fluid dispensing mode of operation of the device may be automatically adjusted based on a sensed position or location of the device and/or base station 130 (e.g., a mobile device). It should be appreciated that the mode of operation may be indicative of one or more fluid dispensing settings of the device, such as, for example, a fluid dispensing volume, a reminder frequency, and more. Accordingly, a mobile application of the mobile device may be configured to determine a current geolocation of the mobile device to activate one of a plurality of modes of operation. It should be understood that the device may include a plurality of fluid dispensing modes stored thereon, each of which may include varying fluid dispensing settings relative to one another.

In some embodiments, a type of trigger received may influence a volume of fluid dispensed from a device. For example, in some embodiments, a number of taps on a tactile trigger of a device may coincide with a volume of fluid to be dispensed from the device (e.g., a higher number of taps corresponds to a greater amount of fluid). In some embodiments, an auditory command may likewise dictate an amount of fluid to be dispensed from the device. In some embodiments, a sensor type detected by the device (or detecting the device) may cause the device to dispense a greater or lesser volume of fluid.

Finally, in some embodiments, a characteristic of a user of a device may influence a volume of fluid dispensed from the device. In some embodiments, a device (e.g., device 200) may be programmed to be used by a specific user. The user may have, e.g., larger or smaller hands than average, and the programming of the device may specify a volume of fluid to be dispensed from device 200 that will suitably sanitize the hands of the user, where a greater volume of fluid is specified for larger hands, and a smaller volume of fluid is specified for smaller hands.

Figure 7:
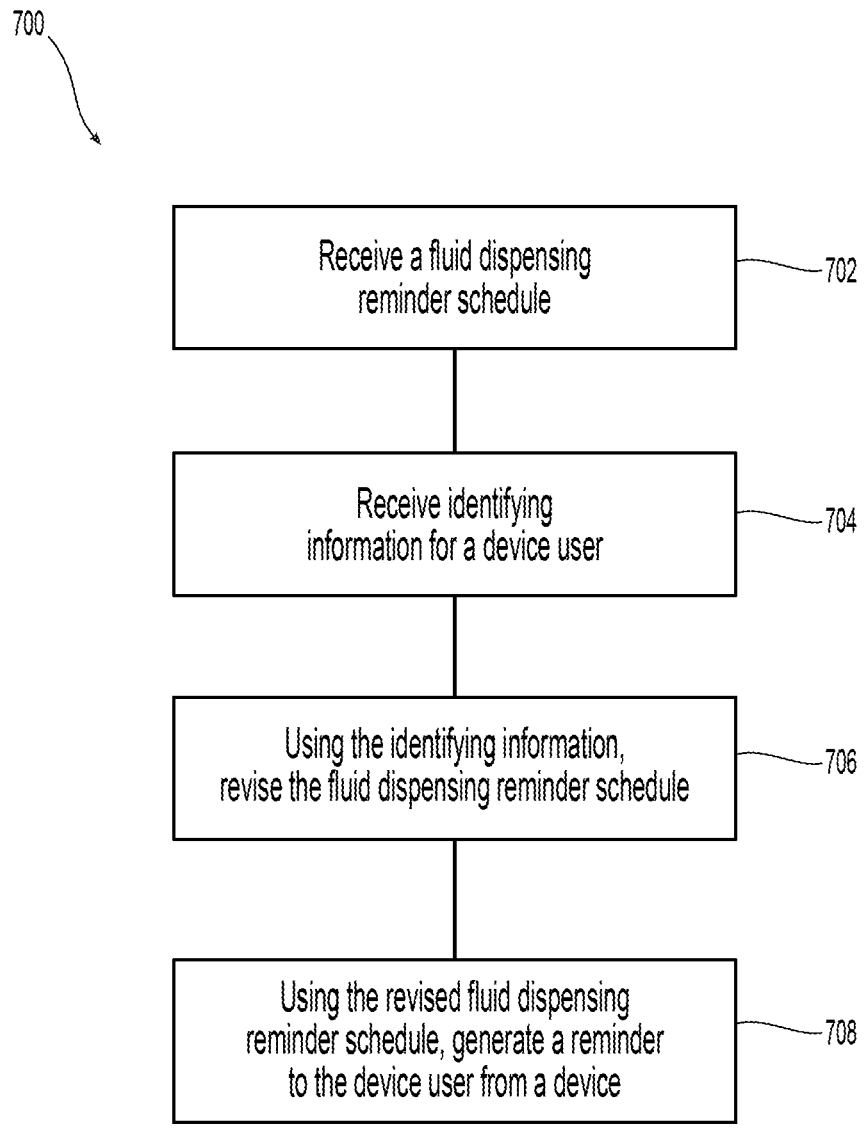
FIG. 7 depicts, in flow chart form, a method of generating a customized fluid dispending reminder schedule, according to aspects of the present disclosure.

FIG. 7 depicts, in flow chart form, a method 700 of generating a customized fluid dispensing reminder schedule, according to aspects of the present disclosure. Method 700 may be performed by any component having a processor within a system including portable fluid dispensing devices (e.g., devices 120, 200, 300), in combination with such devices. For example, method 700 may be performed at or by, e.g., a computer system (e.g., computer system 150), a base station (e.g., base station 130), a personal computer (e.g., personal computer 160), and/or a personal device (e.g., personal device 170), in combination with a portable fluid dispensing device (e.g., devices 120, 200, 300). In some embodiments, method 700 may be performed entirely at or by a portable fluid dispensing device (e.g., devices 120, 200, 300). According to step 702, a fluid dispensing reminder schedule may be received. The schedule may be received at, e.g., a portable fluid dispensing device (e.g., devices 120, 200, 300), or at another device within a system containing portable fluid dispensing devices (e.g., computer system 150, base station 130, personal computer 160, and/or personal device 170). According to step 704, identifying information for a portable device user may be received. The identifying information may be received by, e.g., a processor of the portable device (e.g., processing component 240 of device 200), and/or a processor of a different component of a system including the device (e.g., base station 130, computer system 150, personal computer 160, or personal device 170 of system 100). The identifying information may be any suitable identifying information relevant to tailoring a fluid dispensing reminder schedule to the device user. For example, the identifying information may include a work schedule (e.g., of a device user), a medical procedure schedule (e.g., a surgical procedure) or other events in which the device user may be involved, and/or a physical characteristic of a user of the device. Additionally or alternatively, the identifying information may include characteristics of the device user, such as a hand size measurement of the device user. Such a hand size measurement may include a numeric measurement (e.g., a length, width, or approximate surface area of the hands), or may include a general characterization (e.g., "small," "medium," or "large," etc.).

According to step 706, the fluid dispensing reminder schedule may be revised using the identifying information. This may be performed by, e.g., a processor of the portable device (e.g., processing component 240), and/or a processor of a different component of a system including the device (e.g., base station 130, computer system 150, personal computer 160, or personal device 170 of system 100). Revisions to the schedule may include scheduling extra fluid dispensing reminders, removing fluid dispensing reminders from the schedule, concentrating additional fluid dispensing reminders at a particular time or within a particular time window (e.g., depending on a particular operation, procedure, or sensitive task to be performed at the particular time or within the particular time window), and/or specifying, within the schedule, a recommended volume of fluid to be dispensed when a device is triggered to dispense fluid in response to one or more reminders. In embodiments in which the reminder schedule is not updated at the portable device, the updated reminder schedule may also be forwarded to the device. According to step 708, a reminder may be generated from the portable device to the device user, using the revised fluid dispensing reminder schedule.

Figure 8:
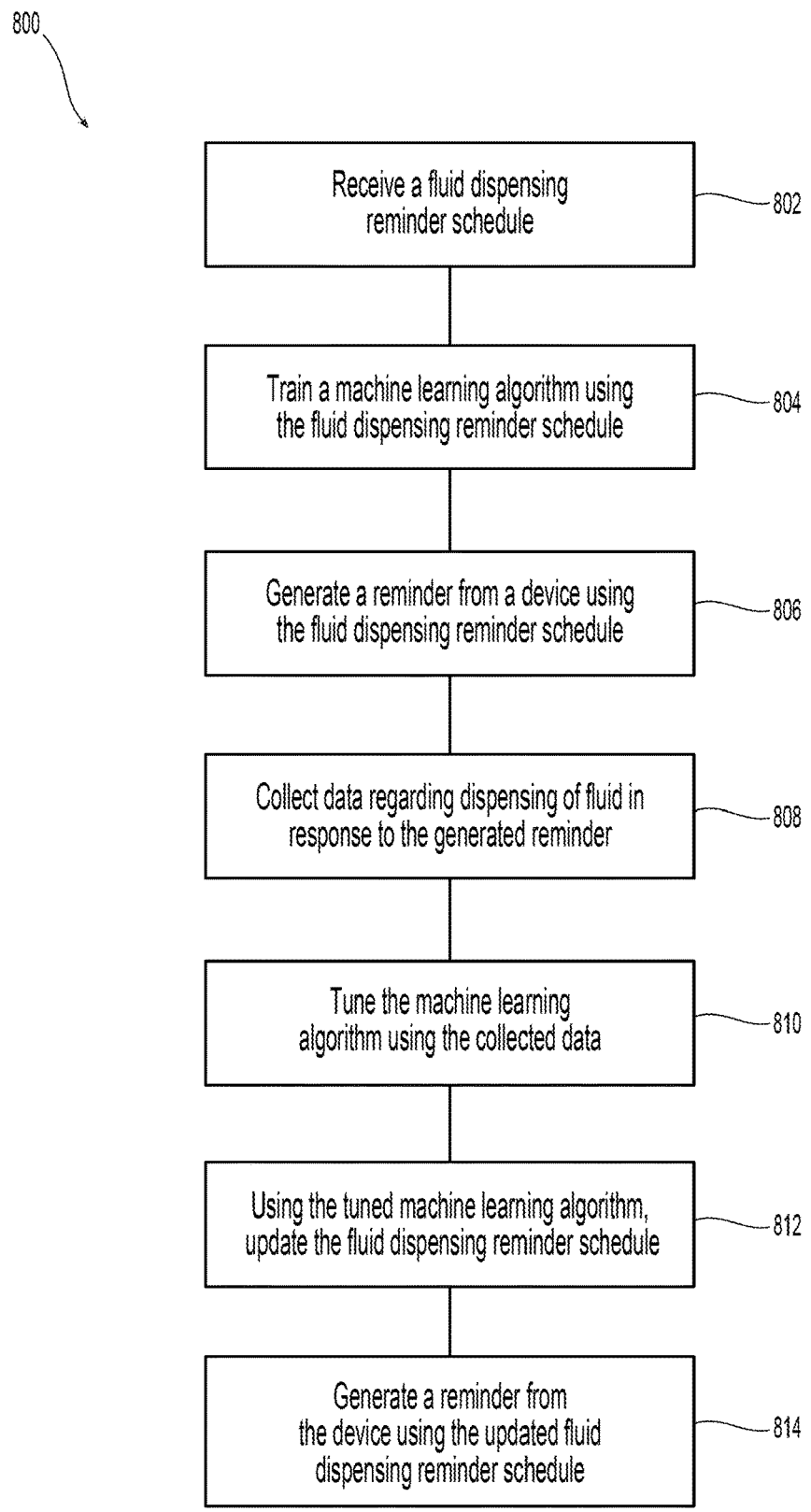
FIG. 8 depicts, in flow chart form, a method of updating a fluid dispensing reminder schedule, according to aspects of the present disclosure.

FIG. 8 depicts, in flow chart form, a method 800 of updating a fluid dispensing reminder schedule, according to aspects of the present disclosure. As is the case with method 700, method 800 may be performed by any component having a processor within a system including portable fluid dispensing devices (e.g., devices 120, 200, 300), in combination with a portable fluid dispensing device. In some embodiments, method 800 may be performed by, e.g., base station 130, computer system 150, personal computer 160, or personal device 170 of system 100, in combination with a portable fluid dispensing device. In some embodiments, method 800 may be performed entirely by a portable fluid dispensing device.

According to step 802, a fluid dispensing reminder schedule may be received. The schedule may be received at, e.g., a portable fluid dispensing device (e.g., devices 120, 200, 300), or at another device within a system containing portable fluid dispensing devices (e.g., computer system 150, base station 130, personal computer 160, and/or personal device 170 of system 100). In some embodiments, multiple fluid dispensing reminder schedules (e.g., pertaining to multiple different fluid dispensing device users) may be received. In such embodiments, the fluid dispensing reminder schedules may be received at, e.g., computer system 150, base station 130, personal computer 160, and/or personal device 170 of system 100. According to step 804, a machine learning algorithm may be trained using the fluid dispensing reminder schedule. The machine learning algorithm may include, e.g., an artificial neural network, such as a recurring neural network or a convolutional neural network, or any other artificial neural network. In embodiments in which multiple fluid dispensing reminder schedules may be received, the machine learning algorithm may be trained using all received fluid dispensing reminder schedules.

According to step 806, a reminder may be generated from a device using the fluid dispensing reminder schedule. For example, a portable fluid dispensing device (e.g., devices 120, 200, 300) may implement the fluid dispensing reminder schedule while an individual is using the device. In some embodiments, multiple reminders may be generated from multiple devices, using multiple fluid dispensing reminder schedules.

According to step 808, data regarding fluid dispensing in response to the generated reminder(s) may be collected. For example, a portable fluid dispensing device generating one or more reminders in accordance with the fluid dispensing reminder schedule may track and/or record whether fluid dispensing is actually triggered in response to each generated reminder. The tracked and/or recorded data may be supplied (e.g., from one device or multiple devices) to the machine learning algorithm.

According to step 810, the machine learning algorithm may be tuned using the collected data. In other words, the machine learning algorithm may compare reminders generated from a portable fluid dispensing device (or devices) to actual dispensing of fluid from a portable fluid dispensing device (or devices), and may "learn" actual device usage habits using such comparisons. In some embodiments, the machine learning algorithm may additionally or alternatively be tuned using other types of data, such as written user schedules, electronic medical records, video records, check-in and check-out logs, etc.

According to step 812, the fluid dispensing reminder schedule may be updated using the tuned machine learning algorithm. Thus, the machine learning algorithm may be used to improve upon a fluid dispensing reminder schedule by providing fluid dispensing reminders that are more attuned to actual responses to such reminders. For example, the machine learning algorithm may find periods of time during which no reminders result in fluid dispensing being triggered, and may identify such periods of time as being periods in which a device user is not required to use the portable fluid dispensing device. Using the machine learning algorithm, a schedule may be updated to stop including reminders during such periods of time. As another example, the machine learning algorithm may identify periods of time during which reminders intermittently result in fluid dispensing being triggered, and may increase a frequency of reminders during such periods of time in a schedule to increase compliance. Advantageously, the incorporation of machine learning algorithms into updating fluid dispensing reminder schedules may result in reminder schedules that more closely adapt to a user's needs, avoid unnecessary reminders, and/or increase compliance with necessary reminders.

Figure 9:
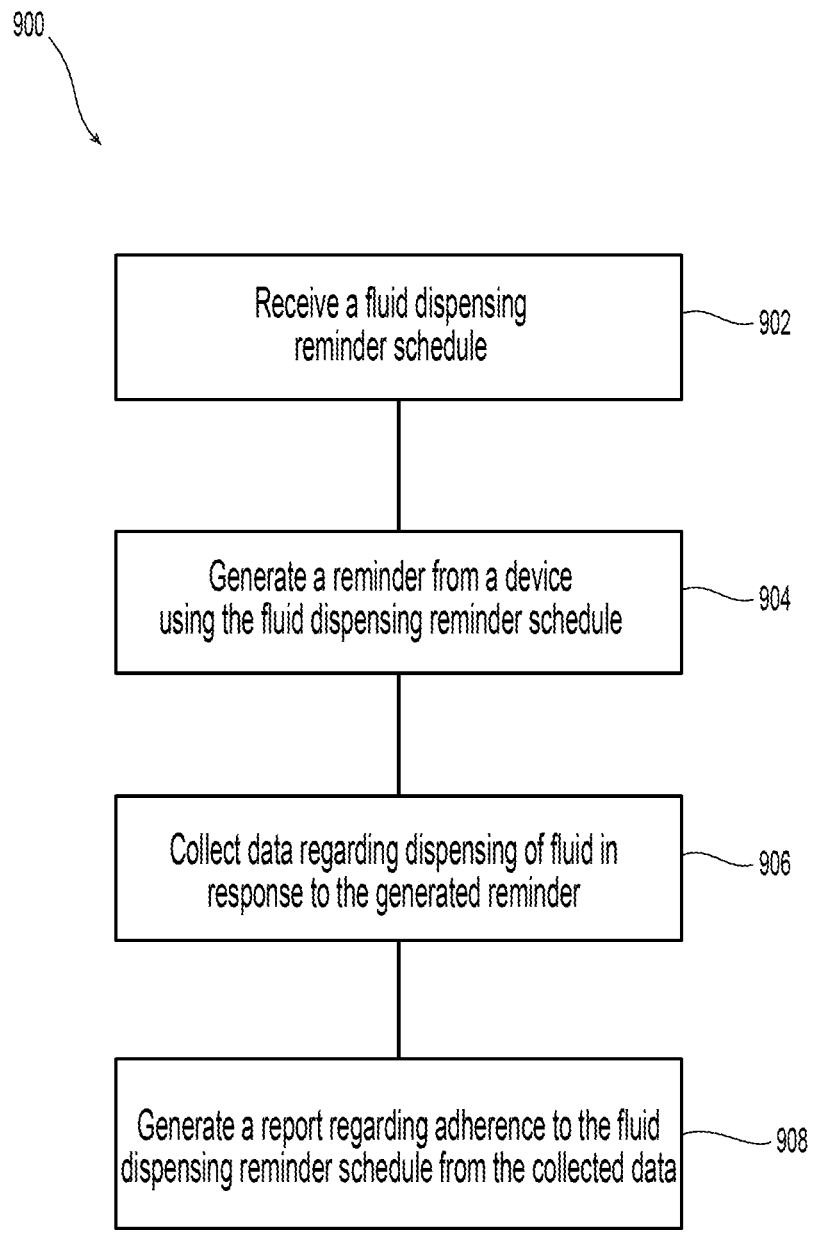
FIG. 9 depicts, in flow chart form, a method of generating a report of adherence to a fluid dispensing reminder schedule, according to aspects of the present disclosure.

FIG. 9 depicts, in flow chart form, a method 900 of generating a report of adherence to a fluid dispensing reminder schedule, according to aspects of the present disclosure. As is the case with methods 700 and 800, method 900 may be performed by any component having a processor within a system including portable fluid dispensing devices (e.g., devices 120, 200, 300), in combination with a portable fluid dispensing device. In particular, method 900 may be performed in part by a component of a system capable of generating reports (e.g., a computer component, such as base station 130, computer system 150, personal computer 160, or personal device 170 of system 100), in combination with a portable fluid dispensing device.

According to step 902, a fluid dispensing reminder schedule may be received. The schedule may be received at, e.g., a portable fluid dispensing device (e.g., devices 120, 200, 300), or at another device within a system containing portable fluid dispensing devices (e.g., computer system 150, base station 130, personal computer 160, and/or personal device 170 of system 100). According to step 904, a reminder may be generated from a device (e.g., a portable fluid dispensing device 120, 200, 300), using the fluid dispensing reminder schedule. According to step 906, data may be collected regarding dispensing of fluid in response to the generated reminder. For example, a portable fluid dispensing device generating one or more reminders in accordance with the fluid dispensing reminder schedule may track and/or record whether dispensing of fluid is actually triggered in response to each generated reminder. The tracked and/or recorded data may be supplied (e.g., from one device or multiple devices) to a device capable of generating a report (e.g., computer system 150, base station 130, personal computer 160, and/or personal device 170 of system 100). According to step 908, a report may be generated regarding adherence to the fluid dispensing reminder schedule from the collected data. To this end, the device capable of generating a report may be programmed with report generation software. In some embodiments, the generated report may include a visual display of the report on a device, such as a computer display. In some embodiments, the generated report may include a catalog of data in, e.g., a spreadsheet, database, or other catalog format. In some embodiments, the generated report may additionally be displayed or provided to a user of a portable fluid dispensing device from which data was collected to create the report. Thus, method 900 may be of use in showing, to a user, an extent to which the user is complying with a fluid dispensing reminder schedule. In still further embodiments, the generated report may be compiled with other such generated reports, and may be provided to an individual, organization, company, and/or institution to show general compliance with fluid dispensing reminder schedules, and to provide a basis for research and development of ways to enhance fluid dispensing reminder schedules or otherwise improve medical institutions, laboratories, and other environments in which fluid dispensing is desired.

The above description and examples are illustrative, and are not intended to be restrictive. One of ordinary skill in the art may make numerous modifications and/or changes without departing from the general scope of the invention. For example, and as has been described, the above-described embodiments (and/or aspects thereof) may be used in combination with each other. Additionally, portions of the above-described embodiments may be removed without departing from the scope of the invention. In addition, modifications may be made to adapt a particular situation or material to the teachings of the various embodiments without departing from their scope. Many other embodiments will also be apparent to those of skill in the art upon reviewing the above description.

What is claimed is:

1. A portable electronic fluid dispensing device, comprising:
    a fluid-containing cartridge;
    a trigger; and
    an electronic pump, comprising:
        a pressure sensor configured to sense a fluid pressure in the cartridge;
        a timer; and
        a pump outlet fluidly connected with an interior of the cartridge, wherein the device is operable independently of a fixed power source.
2. The device of claim 1, wherein the trigger is a tactile trigger and the cartridge is disposable.
3. A system, comprising:
    a plurality of base stations, wherein each base station is paired to a device of claim 1.
4. The system of claim 3, wherein each base station is a mobile device configured to transmit a user command to a device of claim 1 for adjusting one or more settings.
5. The system of claim 3, wherein each base station is configured to receive usage data from a device of claim 1 and to send the usage data to a cloud computing system.
6. The device of claim 5, wherein the base station includes a mobile application configured to compute one or more gel dispensing metrics.
7. The device of claim 1, further comprising:
    a processing component programmed to receive an input from the trigger and, in response, actuate the electronic pump to dispense a volume of fluid from the cartridge.
8. The device of claim 7, wherein the trigger is a tactile trigger, and wherein the input is a number of touches.
9. A method for dispensing sanitization fluid from a portable electronic fluid dispensing device having an electronic pump and a fluid-containing cartridge, the method comprising:
    receiving, at the device, a trigger;
    in response to the received trigger, activating the electronic pump;
    measuring a pressure in the fluid-containing cartridge; and
    deactivating the electronic pump after a time interval,
    wherein the time interval is determined using the measured pressure and an elapsed time since the pump was activated, and wherein the electronic pump, when active for the time interval, causes a predetermined volume of sanitization fluid to be dispensed from the fluid-containing cartridge.
10. The method of claim 9, wherein the trigger includes one of:
    a proximity sensor trigger;
    an auditory cue;
    a motion cue; or
    one or more tactile cues.
11. The method of claim 9, wherein measuring the pressure in the fluid-containing cartridge comprises measuring an increase in pressure caused by the electronic pump.
12. The method of claim 9, wherein the predetermined volume of sanitization fluid is determined using the received trigger.
13. The method of claim 9, further comprising a pressure release valve coupled to the fluid-containing cartridge, wherein the pressure release valve is configured to control the pressure in the fluid-containing cartridge.
14. The method of claim 13, wherein the pressure release valve includes a solenoid configured to generate an electric field or voltage within the fluid-containing cartridge to return an interior of the fluid-containing cartridge to atmospheric pressure.

15. The method of claim 14, wherein the solenoid is configured to activate in response to deactivating the electronic pump after the time interval.

16. A method for updating a fluid dispensing reminder schedule, the method comprising:
   sending, to a portable electronic fluid dispensing device, a first fluid dispensing reminder schedule;
   receiving, from a mobile device, data of a geolocation of the mobile device;
   tuning a machine learning algorithm using the received data;
   using the tuned machine learning algorithm, updating the fluid dispensing reminder schedule; and
   sending, to the portable electronic fluid dispensing device, the updated fluid dispensing reminder schedule.

17. The method of claim 16, wherein the data of the geolocation is indicative of a high-risk area such that tuning the machine learning algorithm includes increasing a frequency of reminders included in the fluid dispensing reminder schedule.

18. The method of claim 16, wherein the data of the geolocation is indicative of a low-risk area such that tuning the machine learning algorithm includes decreasing a frequency of reminders included in the fluid dispensing reminder schedule.

19. The method of claim 16, further comprising:
   sending, to the portable electronic fluid dispensing device, a plurality of fluid dispensing modes, each of the fluid dispensing modes include one or more settings;
   receiving, from the mobile device, data of the geolocation of the mobile device;
   activating at least one of the plurality of fluid dispensing modes on the portable electronic fluid dispensing device based on the received data; and
   changing the one or more settings of the portable electronic fluid dispensing device based on the at least one of the plurality of fluid dispensing modes.

20. The method of claim 19, wherein the one or more settings include a fluid dispensing volume and a fluid dispensing reminder.

* * * * *